US010202649B2

(12) United States Patent
Patel et al.

(10) Patent No.: US 10,202,649 B2
(45) Date of Patent: Feb. 12, 2019

(54) DETECTION OF TRAUMATIC BRAIN INJURY

(71) Applicant: The University of Montana, Missoula, MT (US)

(72) Inventors: Sarjubhai Patel, Missoula, MT (US); Thomas Rau, Stevensville, MT (US)

(73) Assignee: The University of Montana, Missoula, MT (US)

(*) Notice: Subject to any disclaimer, the term of this patent is extended or adjusted under 35 U.S.C. 154(b) by 0 days.

(21) Appl. No.: 15/432,172

(22) Filed: Feb. 14, 2017

(65) Prior Publication Data

US 2017/0268058 A1  Sep. 21, 2017

Related U.S. Application Data

(63) Continuation of application No. 14/669,454, filed on Mar. 26, 2015, now Pat. No. 9,605,315.

(60) Provisional application No. 61/970,613, filed on Mar. 26, 2014.

(51) Int. Cl.
| | |
|---|---|
| *A61K 48/00* | (2006.01) |
| *C07H 21/02* | (2006.01) |
| *C07H 21/04* | (2006.01) |
| *C12Q 1/6883* | (2018.01) |

(52) U.S. Cl.
CPC ...... *C12Q 1/6883* (2013.01); *C12Q 2600/112* (2013.01); *C12Q 2600/118* (2013.01); *C12Q 2600/158* (2013.01); *C12Q 2600/178* (2013.01)

(58) Field of Classification Search
CPC .............................. C12N 15/111; C12N 15/113
See application file for complete search history.

(56) References Cited

U.S. PATENT DOCUMENTS

| | | | |
|---|---|---|---|
| 6,821,985 B2 | 11/2004 | Chenard et al. | |
| 2011/0111976 A1 | 5/2011 | Fare et al. | |
| 2013/0022982 A1 | 1/2013 | Wang et al. | |

FOREIGN PATENT DOCUMENTS

| | | |
|---|---|---|
| WO | WO 2011/032155 A2 | 3/2011 |
| WO | WO 2011/149354 A1 | 12/2011 |
| WO | 2013036993 A1 | 3/2013 |
| WO | WO 2013/032962 A2 | 3/2013 |

OTHER PUBLICATIONS

Purow, J Neurooncol. Jul. 2011 ; 103(3): 429-436.*
Ferretti et al. (Int. J. Cancer: 124, 568-577, 2009).*
Balakathiresan et al. (Journal of Neurotrauma 29:1379-1387 (May 1, 2012)).*
Birks, et al., "Survey of microRNA Expression in Pediatric Brain Tumors," *Pediatr Blood Cancer* 56:211-216 (2011).
Lei, et al., "Microarray Based Analysis of microRNA Expression in Rat Cerebral Cortex After Traumatic Brain Injury," *Brain Res.* 1284:191-201 (2009).

Salmaso, et al., "Targeting Glioma Cells in Vitro With Ascorbate-Conjugated Pharmaceutical Nanocarriers," *Bioconjug Chem* 20(12):2348-2355 (2009).
Shende, et al., "microRNAs Function As Cis- and Trans-Acting Modulators of Peripheral Circadian Clocks," *FEBS Letters* 588:3015-3022 (2014).
Hall, et al., "Antioxidant Therapies for Traumatic Brain Injury," Neurotherapeutics, vol. 7, No. 1, pp. 51-61 (2010).
Redell, et al., "Human Traumatic Brain Injury Alters Plasma microRNA Levels," Journal of Neurotrauma, vol. 27, No. 12, DOI:10.1089/NEU.2010.1481, pp. 2147-2156 (2010).
Sharma, et al., "Identification of Serum microRNA Signatures for Diagnosis of Mild Traumatic Brain Injury in a Closed Head Injury Model," PLOS One, vol. 9, Issue 11, e112019, 20 pgs. (2014).
Sun, et al., "Expression Profiling of microRNAs in Hippocampus of Rats Following Traumatic Brain Injury," Journal of Huazhong University of Science and Technology [Medical Sciences], vol. 34, Issue 4, DOI:10.1007/s11596-014-1313-1, pp. 548-553 (2014).
Supplementary Partial European Search Report and Provisional Opinion Accompanying the Partial Search Report issued in corresponding EP Patent Application No. 15886700.2 dated Jun. 28, 2018, 14 pgs.
Wang, et al., "Mitochondria-Associated microRNAs in Rat Hippocampus Following Traumatic Brain Injury," Experimental Neurology, vol. 265, pp. 84-93 (2005).
Communication re Extended European Search Report in related EP Patent Application No. 15886700.2 dated Sep. 25, 2018 accompanied by Supplementary European Search Report dated Sep. 17, 2018, 9 pages.
Hoss, "Microras Located in the Hox Gene Clusters Are Implicated in Huntigton's Disease Pathogenesis," PLOS Genetics, vol. 10, No. 2, p. e1004188 (2014).
Hu, et al. "Expression Profile of Micrornas in Rat Hippocampus Following Lithium-Pilocarpine-Induced Status Epilepticus," Neuroscience Letters, vol. 488, No. 3, pp. 252-257 (2011).
Liu, et al. "Micrornas Involved in Regulating Spontaneous Recovery in Embolic Stroke Model," including Supplementary Material, PLOS One, vol. 8, No. 6, p. e66393, URL:https://doi.org/10.1371/Journal.pomme 0066393.s001 (2014).
Lusardi, et al. "Ischemic Preconditioning Regulates Expression of Micrornas and a Predicted Target, MECP2, in Mouse Cortex," Journal of Cerebral Blood Flow & Metabolism, vol. 30, No. 4, pp. 744-756 (2009).
Shirley, et al. "Oxidative Stress and the Use of Antioxidants in Stroke," Antioxidants, vol. 3, No. 3, pp. 479-501 (2014).

* cited by examiner

*Primary Examiner* — Amy H Bowman
(74) *Attorney, Agent, or Firm* — Pasternak Patent Law

(57) ABSTRACT

The present invention provides minimally invasive methods of detecting, diagnosing, and assessing neuronal damage associated with traumatic brain injury (TBI) or chronic traumatic encephalopathy (CTE). Specific species of microRNAs (miRNA), small, noncoding RNA molecules that play gene regulatory functions, are correlated with cellular damage and oxidative stress following TBI or CTE, allowing for rapid, minimally-invasive diagnosis and assessment of brain injury. The early identification and longitudinal assessment of neuronal damage in subjects suffering from or at risk of suffering from a TBI (e.g., football players, boxers, military personnel, fall victims) will improve clinical outcomes by guiding critical medical and behavioral decision making.

17 Claims, 12 Drawing Sheets
Specification includes a Sequence Listing.

FIG.1 (A-D)

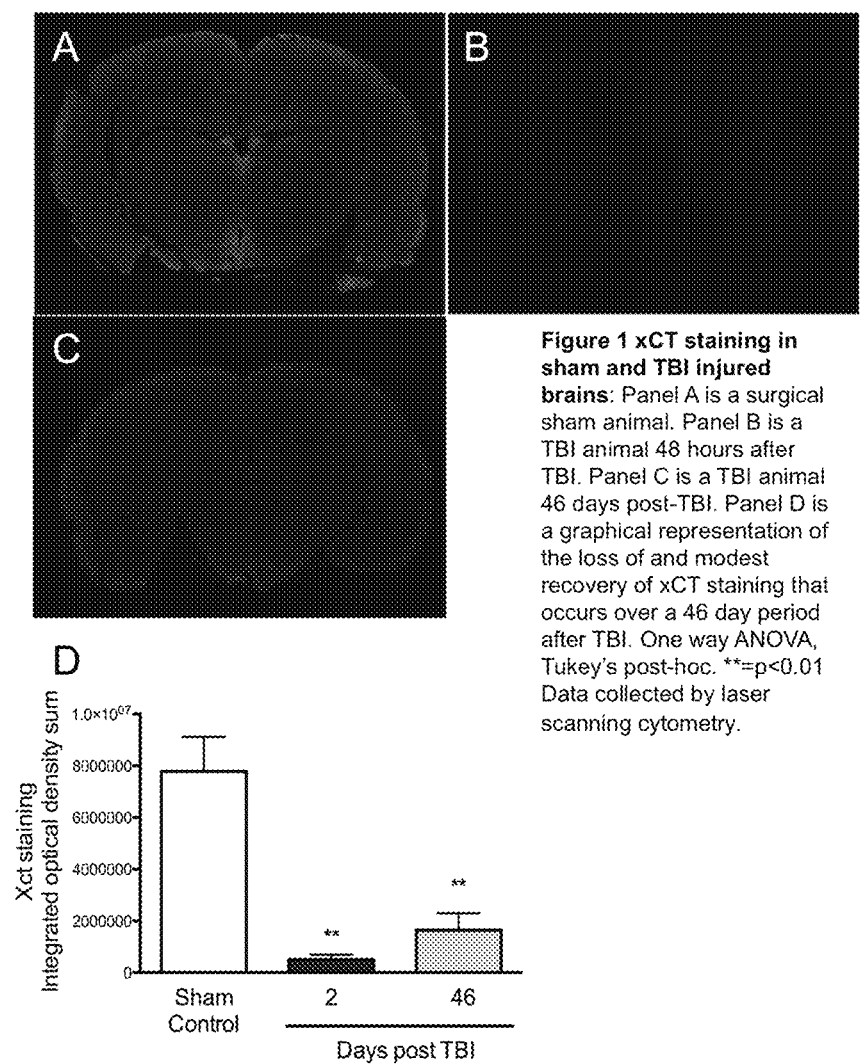

Figure 1 xCT staining in sham and TBI injured brains: Panel A is a surgical sham animal. Panel B is a TBI animal 48 hours after TBI. Panel C is a TBI animal 46 days post-TBI. Panel D is a graphical representation of the loss of and modest recovery of xCT staining that occurs over a 46 day period after TBI. One way ANOVA, Tukey's post-hoc. **=p<0.01 Data collected by laser scanning cytometry.

FIG. 2 (Panels E and F)
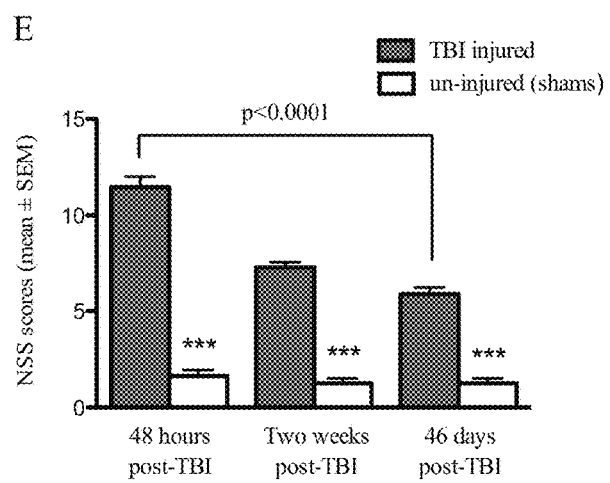
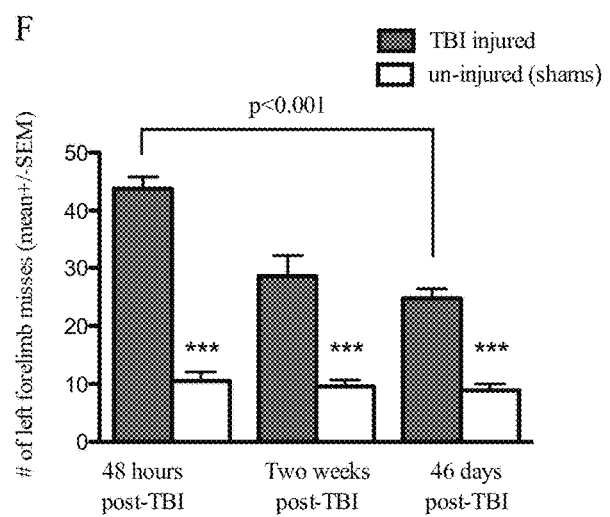

FIG. 3 (Panels A-D)
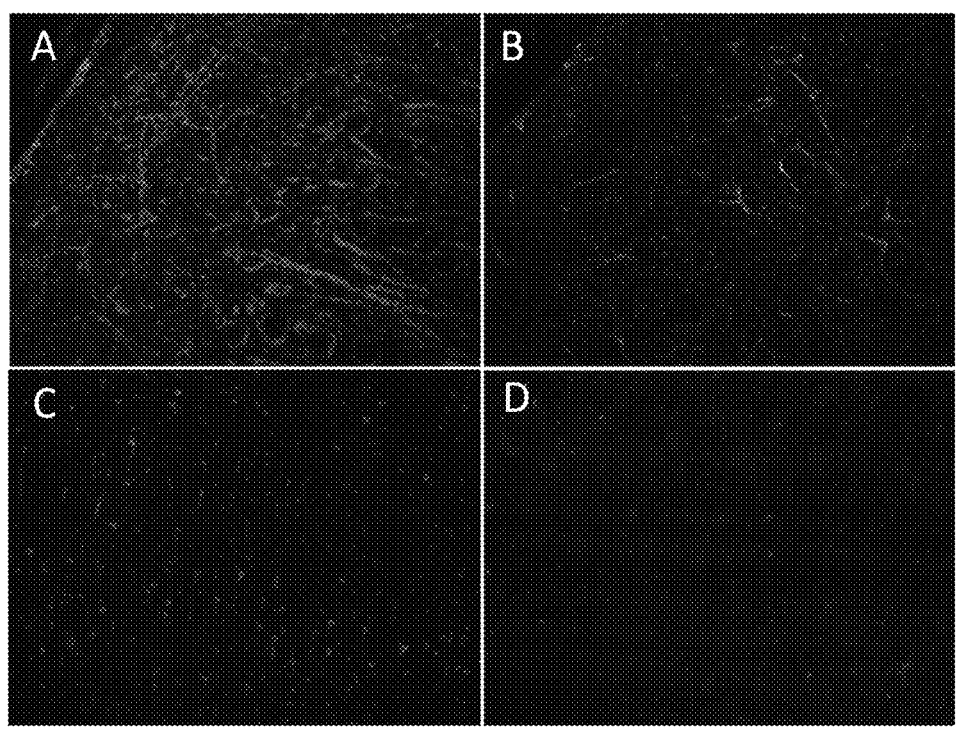

FIG. 6

PCR Array CMIHS02277

| Position | Mature ID |
|---|---|
| A01-A24 | hsa-miR-142-3p* |
| B01-B24 | hsa-let-7f-5p* |
| C01-C24 | hsa-miR-144-3p* |
| D01-D24 | hsa-miR-150-5p* |
| E01-E24 | hsa-miR-223-3p |
| F01-F24 | hsa-miR-196b-5p* |
| G01-G24 | hsa-miR-423-3p |
| H01-H24 | hsa-miR-182-3p* |
| I01-I24 | hsa-miR-196a-5p* |
| J01-J24 | hsa-miR-32-5p* |
| K01-K24 | hsa-miR-9-5p |

* Predicted to target xCT (*SLC7A11*)

FIG. 7

Control v Acute TBI

|  | Fold Change | 95% CI | p-value |
|---|---|---|---|
| hsa-miR-142-3p | 3.6121 | ( 0.00001, 10.41 ) | 0.049554 |
| hsa-let-7f-5p | 1.6885 | ( 0.00001, 4.79 ) | 0.139947 |
| hsa-miR-144-3p | 0.6695 | ( 0.21, 1.13 ) | 0.425351 |
| hsa-miR-150-5p | 0.8271 | ( 0.00001, 2.09 ) | 0.03043 |
| hsa-miR-223-3p | 2.1864 | ( 0.00001, 7.53 ) | 0.063883 |
| hsa-miR-196b-5p | 2.2423 | ( 0.00001, 6.29 ) | 0.027461 |
| hsa-miR-423-3p | 3.2944 | ( 0.00001, 7.77 ) | 0.790478 |
| hsa-miR-182-3p | 1.1189 | ( 0.73, 1.51 ) | 0.086503 |
| hsa-miR-196a-5p | 2.1676 | ( 0.00001, 5.92 ) | 0.30099 |
| hsa-miR-32-5p | 1.1206 | ( 0.00001, 2.50 ) | 0.790478 |
| hsa-miR-9-5p | 1.1189 | ( 0.73, 1.51 ) | 0.596262 |

FIG. 8

Control v Football

|  | Fold Change | 95% CI | p-value |
|---|---|---|---|
| hsa-miR-142-3p | 2.833 | ( 1.05, 4.61 ) | 0.596178 |
| hsa-let-7f-5p | 2.1295 | ( 0.81, 3.45 ) | 0.596038 |
| hsa-miR-144-3p | 1.3769 | ( 0.35, 2.40 ) | 0.595357 |
| hsa-miR-150-5p | 1.4645 | ( 0.55, 2.37 ) | 0.596662 |
| hsa-miR-223-3p | 2.6715 | ( 0.78, 4.56 ) | 0.596143 |
| hsa-miR-196b-5p | 2.0135 | ( 1.03, 2.99 ) | 0.584311 |
| hsa-miR-423-3p | 2.1985 | ( 1.09, 3.31 ) | 0.595836 |
| hsa-miR-182-3p | 1.2916 | ( 0.77, 1.81 ) | 0.596435 |
| hsa-miR-196a-5p | 1.7157 | ( 0.79, 2.64 ) | 0.593373 |
| hsa-miR-32-5p | 1.2295 | ( 0.52, 1.94 ) | 0.596625 |
| hsa-miR-9-5p | 1.3262 | ( 0.79, 1.86 ) | 0.596262 |

FIG. 9

Football v Acute

|  | Fold Change | 95% CI | p-value |
|---|---|---|---|
| hsa-miR-142-3p | 1.275 | ( 0.00001, 3.68 ) | 0.780055 |
| hsa-let-7f-5p | 0.7929 | ( 0.00001, 2.25 ) | 0.779346 |
| hsa-miR-144-3p | 0.4862 | ( 0.21, 0.76 ) | 0.775941 |
| hsa-miR-150-5p | 0.5647 | ( 0.00001, 1.42 ) | 0.778829 |
| hsa-miR-223-3p | 0.8184 | ( 0.00001, 2.80 ) | 0.780531 |
| hsa-miR-196b-5p | 1.1137 | ( 0.00001, 3.16 ) | 0.792831 |
| hsa-miR-423-3p | 1.4984 | ( 0.00001, 3.57 ) | 0.781275 |
| hsa-miR-182-3p | 0.8663 | ( 0.49, 1.24 ) | 0.778034 |
| hsa-miR-196a-5p | 1.2634 | ( 0.00001, 3.46 ) | 0.791925 |
| hsa-miR-32-5p | 0.9114 | ( 0.00001, 2.06 ) | 0.77859 |
| hsa-miR-9-5p | 0.8437 | ( 0.48, 1.21 ) | 0.777932 |

FIG. 10

Control v Soccer

|              | Fold Change | 95% CI        | p-value  |
|--------------|-------------|---------------|----------|
| hsa-miR-142-3p | 2.8806    | ( 1.03, 4.73 ) | 0.159849 |
| hsa-let-7f-5p  | 1.7008    | ( 0.72, 2.68 ) | 0.022646 |
| hsa-miR-144-3p | 0.6255    | ( 0.19, 1.06 ) | 0.121517 |
| hsa-miR-150-5p | 0.81      | ( 0.38, 1.24 ) | 0.023897 |
| hsa-miR-223-3p | 2.7636    | ( 0.90, 4.62 ) | 0.237895 |
| hsa-miR-196b-5p | 1.218    | ( 0.81, 1.63 ) | 0.035004 |
| hsa-miR-423-3p | 1.8817    | ( 1.04, 2.72 ) | 0.638166 |
| hsa-miR-182-3p | 1.0861    | ( 0.79, 1.38 ) | 0.666806 |
| hsa-miR-196a-5p | 1.0808   | ( 0.62, 1.54 ) | 0.493646 |
| hsa-miR-32-5p  | 1.0496    | ( 0.50, 1.59 ) | 0.347194 |
| hsa-miR-9-5p   | 1.1564    | ( 0.81, 1.50 ) | 0.596262 |

FIG. 11

Control v Chronic TBI

|  | Fold Change | 95% CI | p-value |
|---|---|---|---|
| hsa-miR-142-3p | 0.8327 | ( 0.24, 1.42 ) | 0.72905 |
| hsa-let-7f-5p | 0.6456 | ( 0.00001, 1.44 ) | 0.206123 |
| hsa-miR-144-3p | 0.6279 | ( 0.04, 1.22 ) | 0.270062 |
| hsa-miR-150-5p | 0.7395 | ( 0.22, 1.26 ) | 0.322192 |
| hsa-miR-223-3p | 0.6505 | ( 0.00001, 1.35 ) | 0.097407 |
| hsa-miR-196b-5p | 1.8213 | ( 0.00001, 4.53 ) | 0.849861 |
| hsa-miR-423-3p | 0.9876 | ( 0.34, 1.64 ) | 0.622911 |
| hsa-miR-182-3p | 0.907 | ( 0.51, 1.30 ) | 0.992248 |
| hsa-miR-196a-5p | 1.11 | ( 0.27, 1.95 ) | 0.094796 |
| hsa-miR-32-5p | 3.9103 | ( 0.00001, 19.26 ) | 0.548913 |
| hsa-miR-9-5p | 1.0936 | ( 0.47, 1.72 ) | 0.596262 |

FIG. 12

Acute v Chronic

|  | Fold Change | 95% CI | p-value |
|---|---|---|---|
| hsa-miR-142-3p | 0.2305 | ( 0.00001, 0.67 ) | 0.180587 |
| hsa-let-7f-5p | 0.3824 | ( 0.00001, 1.19 ) | 0.224117 |
| hsa-miR-144-3p | 0.9379 | ( 0.18, 1.69 ) | 0.742084 |
| hsa-miR-150-5p | 0.8941 | ( 0.00001, 2.28 ) | 0.430334 |
| hsa-miR-223-3p | 0.2975 | ( 0.00001, 1.06 ) | 0.204429 |
| hsa-miR-196b-5p | 0.8123 | ( 0.00001, 2.69 ) | 0.818098 |
| hsa-miR-423-3p | 0.2998 | ( 0.00001, 0.73 ) | 0.221697 |
| hsa-miR-182-3p | 0.8106 | ( 0.43, 1.19 ) | 0.445785 |
| hsa-miR-196a-5p | 0.5121 | ( 0.00001, 1.44 ) | 0.326865 |
| hsa-miR-32-5p | 3.4895 | ( 0.00001, 17.73 ) | 0.407382 |
| hsa-miR-9-5p | 0.9774 | ( 0.40, 1.56 ) | 0.795451 |

DETECTION OF TRAUMATIC BRAIN INJURY

CROSS-REFERENCE TO RELATED APPLICATIONS

This application is a continuation of U.S. Non-Provisional patent application Ser. No. 14/669,454, filed Mar. 26, 2015, which claims the benefit of the filing date of U.S. Provisional Patent Application Ser. No. 61/970,613, filed Mar. 26, 2014, the disclosures of which are incorporated by reference in their entirety.

REFERENCE TO SEQUENCE LISTING

This application includes as part of the originally filed subject matter a Sequence Listing electronically submitted via EFS-Web as a single text file named "UM014003SL.txt". The Sequence Listing text file was created on Feb. 14, 2017 and is 14 kb in size. The contents of the Sequence Listing are hereby incorporated by reference.

BACKGROUND OF THE INVENTION

The acute and chronic molecular effects of mild TBI (mTBI) have not been well studied or characterized. Over the past several decades it has become increasingly clear that repetitive mTBI is capable of altering the biochemical activity of the brain in ways that cannot be detected by current methodologies. Highlighting this issue is the definitive link between repeated mTBI and the development of chronic traumatic encephalopathy (CTE) in athletes and soldiers. The immediate issue facing an individual that has suffered a mTBI is determining when it is safe to return to high risk activities after a concussive injury without risking permanent brain damage that occurs at a cellular level. Unfortunately, no non-invasive diagnostic methods or tools currently exist to evaluate TBI-caused neuronal damage or CTE progression.

MicroRNAs ("miRNAs") are endogenous, non-coding small RNAs approximately 22 base pair in length. MiRNAs are highly conserved across species, accounting for 1-2% of the genes in eukaryotic genomes while potentially regulating 30% of all annotated human genes. Mature miRNAs bind sequence-specific sites in the 3'-untranslated region (3'-UTR) of their target mRNAs and inhibit protein synthesis by repressing translation or regulating mRNA degradation. Some single miRNA have been predicted to regulate several hundred-target mRNAs. MiRNAs are important epigenetic regulators of biological processes and many are expressed specifically in an organ, cell or cellular compartment. The discovery that circulating miRNAs are altered in pathological conditions has spawned the development of miRNAs as potential biomarkers of neurodegenerative diseases. The release of miRNAs whether passive, associated with Argonaut2 (ago2) or mediated by active secretion via exosomes or microvesicles is believed to dramatically effect protein expression throughout the central nervous system. In the case of CTE, the definitive diagnosis of the disease is made post-mortem by the identification of neuronal death in specific areas of the brain e.g., cerebral hemispheres, thalamus and medial temporal lobe. However profound loss of neurons and brain atrophy are late-occurring events in the pathogenesis of the disease and are preceded by metabolic changes such as hyperphosphorylation of tau and deposition of neurofibrillary tangles presumably leading to synaptic dysfunction and loss, neurite retraction and axonal degeneration. Such damage has been demonstrated to release stable miRNA into the systemic circulation.

SUMMARY OF THE INVENTION

The present invention features methods and kits useful for the minimally invasive detection of brain injury. In a first aspect, the invention provides a method of detecting a brain injury in a patient, such as a human, by contacting a biological sample derived from the patient with at least one miR-specific oligodeoxynucleotide probe having at least 70% complementarity to a sequence selected from SEQ ID NOs. 1-69, determining the expression level of at least one microRNA represented by SEQ ID NOs. 1-69 by quantifying at least one such miR-specific oligodeoxynucleotide probe, and comparing the expression level with a control expression level derived from a healthy subject, wherein a 1.2 fold or greater difference between the patient and control microRNA expression levels indicates that the patient has suffered a brain injury. In one embodiment, the method further provides for the treatment of the patient with a therapeutically-effective amount of an antioxidant, such as alpha-tocopherol, ascorbate, coenzyme Q, alpha-lipoic acid, curcumin, glutathione, uric acid, a carotene, superoxide dismutase, a catalase, a peroxiredoxin, a thioredoxin, tirilazad mesylate, or NXY-059, if brain injury is detected. In another embodiment, the biological sample is blood, cerebral spinal fluid, brain tissue. In a further embodiment, the biological sample is blood plasma or serum. The method can be used to detect brain injuries such as traumatic brain injury and chronic traumatic encephalopathy. The method can be performed using polymerase chain reaction (PCR), in situ hybridization, Northern blot, or gene chip analysis using, e.g., DNA oligonucleotide probes. In one embodiment, the biological sample is derived before the patient has suffered a brain injury. In another embodiment, the method is repeated on biological samples derived from the patient over a period of time to allow for measurement of brain injury progression or healing.

In a second aspect, the invention provides a minimally-invasive method of detecting a brain injury in a patient, such as a human, by contacting a blood, plasma, or serum sample derived from the patient with at least one miR-specific oligodeoxynucleotide probe having at least 70% complementarity to a sequence selected from SEQ ID NOs. 1-69, determining the expression level of at least one microRNA represented by SEQ ID NOs. 1-69 by quantifying at least one such miR-specific oligodeoxynucleotide probe, and comparing the expression level with a control expression level derived from a healthy subject, wherein a 1.2 fold or greater difference between the patient and control microRNA expression levels indicates that the patient has suffered a brain injury. In one embodiment, the method further provides for the treatment of the patient with a therapeutically-effective amount of an antioxidant.

In a third aspect, the invention provides a kit detecting a brain injury that includes (a) one or more miR-specific oligonucleotide probes having at least 70% complementarity to a sequence selected from SEQ ID NOs. 1-69, (b) one or more control samples, and (c) instructions indicating the use of the probes and control samples for detecting a brain injury.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

As used herein, the singular form "a," "an," and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the terms below have the meanings indicated.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from abnormal (e.g., diseased or injured) tissue, and within abnormal tissue, different prognosis states (for example, good or poor long term survival prospects) may be determined. By comparing expression profiles of tissue (e.g., blood, tissue biopsy or necropsy sample, or cerebral spinal fluid) in different states, information regarding which genes are important (including both up- and down-regulation of genes) in each of these states is obtained. The identification of sequences that are differentially expressed in tissue, as well as differential expression resulting in different prognostic outcomes, allows the use of this information in a number of ways. For example, a particular treatment regime may be evaluated (e.g., to determine whether a therapeutic drug acts to improve the long-term prognosis in a particular patient). Similarly, diagnosis may be done or confirmed by comparing patient samples with known expression profiles. Furthermore, these gene expression profiles (or individual genes) allow screening of drug candidates that alter or normalize tissue expression profiles to impart a clinical benefit.

The term "imaging agent" as used herein refers to any moiety useful for the detection, tracing, or visualization of a compound when coupled thereto. Imaging agents include, e.g., an enzyme, a fluorescent label (e.g., fluorescein), a luminescent label, a bioluminescent label, a magnetic label, a metallic particle (e.g., a gold particle), a nanoparticle, an antibody or fragment thereof (e.g., a Fab, Fab', or F(ab')$_2$ molecule), and biotin. An imaging agent can be coupled to a compound by, for example, a covalent bond, ionic bond, van der Waals interaction or a hydrophobic bond. An imaging agent can be a radiolabel coupled to or a radioisotope incorporated into the chemical structure of a compound used according to the invention. Methods of detecting such imaging agents include, but are not limited to, positron emission tomography (PET), X-ray computed tomography (CT) and magnetic resonance imaging (MRI).

As used herein interchangeably, a "miR gene product," "microRNA," "miR," or "miRNA" refers to the unprocessed (e.g., precursor) or processed (e.g., mature) RNA transcript from a miR gene. As the miR gene products are not translated into protein, the term "miR gene products" does not include proteins. The unprocessed miR gene transcript is also called a "miR precursor" or "miR prec" and typically comprises an RNA transcript of about 70-100 nucleotides in length. The miR precursor can be processed by digestion with an RNAse (for example, Dicer, Argonaut, or RNAse III (e.g., E. coli RNAse III)) into an active 19-25 nucleotide RNA molecule. This active 19-25 nucleotide RNA molecule is also called the "processed" miR gene transcript or "mature" miRNA.

The term "neurodegenerative disorder" as used herein, refers to any disease, disorder, condition, or symptom characterized by the structural or functional loss of neurons. Neurodegenerative disorders include, e.g., Alzheimer's disease, Parkinson's disease, Huntington's Disease, Lewy Body dementia, and amyotrophic lateral sclerosis (ALS).

As used herein, "probe oligonucleotide" or "probe oligodeoxynucleotide" refers to an oligonucleotide that is capable of hybridizing to a target oligonucleotide. By "miR-specific oligonucleotide probe" or "probe oligonucleotide specific for a miR" is meant a probe oligonucleotide that has a sequence selected to hybridize to a specific miR gene product, or to a reverse transcript of the specific miR gene product.

"Target oligonucleotide" or "target oligodeoxynucleotide" refers to a molecule to be detected (e.g., via hybridization).

As used herein, "sample" refers to any biological matter derived from a subject (e.g., a human). Samples include, but are not limited to, blood, PBMC, plasma, platelets, serum, cerebral spinal fluid (CSF), saliva, cells, tissues, and organs. In certain embodiments of the invention, preferred samples include blood plasma, CSF, and brain tissue.

The phrase "therapeutically effective" is intended to qualify the amount of active ingredients used in the treatment of a disease or disorder. This amount will achieve the goal of reducing or eliminating the disease or disorder.

The term "therapeutically acceptable" refers to those compounds (or salts, esters, prodrugs, tautomers, zwitterionic forms, etc. thereof) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means mammals and non-mammals. Mammals means any member of the mammalian class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "patient" does not denote a particular age or sex.

The term "prodrug" refers to a compound that is made more active in vivo. Certain compounds may also exist as prodrugs, as described in *Hydrolysis in Drug and Prodrug Metabolism: Chemistry, Biochemistry, and Enzymology*, Testa, Bernard and Wiley-VHCA, Zurich, Switzerland 2003. Prodrugs of the compounds are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bio-available by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug is a compound that is administered as an ester (the "prodrug"), but then is metabolically hydrolyzed to the carboxylic acid, the active entity. Additional examples include peptidyl derivatives of a compound.

Compounds can exist as therapeutically acceptable salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Stahl, P. Heinrich, *Pharmaceutical Salts: Properties, Selection, and Use*, Wiley-VCHA, Zurich, Switzerland (2002).

The term "therapeutically acceptable salt" as used herein, represents salts or zwitterionic forms of a compound which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion.

BRIEF DESCRIPTION OF THE DRAWINGS

FIG. 1 shows System xCT staining in sham and TBI-injured brains. Panel A is a surgical sham animal. Panel B is a TBI animal 48 hours after TBI. Panel C is a TBI animal 46 days post-TBI. Panel D is a graphical representation of the loss of and modest recovery of xCT straining that occurs over a 46 day period after TBI. One way ANOVA, Tukey's post-hoc. **=p<0.01. Data collected by laser scanning cytometry.

FIG. 2 panels E and F show neurological severity scores and foot faults, respectively, from injured and un-injured animals at 48 hours, 2 weeks, and 46 days post-TBI. In both assessments there was a significant improvement from 48 hours to 46 days post-TBI that corresponds with the return of xCT to the neuromotor cortex. However, neurological scoring remained significantly lower than shams that had normal levels of xCT expression. n=12 animals per group; unpaired two-tailed t-test. ***=p<0.001.

FIG. 3 shows System xCT (red) and GFAP (green) staining in the cortex of rats and human patients. Panel A is a surgical sham rat. Panel B is a TBI rat 46 days after injury. Panel C is a human control patient. Panel D is a stage IV CTE patient. Data collected at 60× using an Olympus FV1000 confocal microscope. Human tissue was kindly provided by the Center for the Study of Traumatic Encephalopathy (Boston University).

FIG. 6 is a chart of miRNA probes used in PCR Array CMIHS02277. *=predicated to target xCT (SLC7A11).

FIG. 7 is a chart showing the fold change, 95% confidence interval, and p values between miRNA expression profiles on the PCR Array CMIHS02277 between human peripheral blood plasma obtained from control subjects and those having suffered acute TBI (within 24-72 hours).

FIG. 8 is a chart showing the fold change, 95% confidence interval, and p values between miRNA expression profiles on the PCR Array CMIHS02277 between human peripheral blood plasma obtained from control subjects and football players.

FIG. 9 is a chart showing the fold change, 95% confidence interval, and p values between miRNA expression profiles on the PCR Array CMIHS02277 between human peripheral blood plasma obtained from football players and those having suffered acute TBI (within 24-72 hours).

FIG. 10 is a chart showing the fold change, 95% confidence interval, and p values between miRNA expression profiles on the PCR Array CMIHS02277 between human peripheral blood plasma obtained from control subjects and soccer players.

FIG. 11 is a chart showing the fold change, 95% confidence interval, and p values between miRNA expression profiles on the PCR Array CMIHS02277 between human peripheral blood plasma obtained from control subjects and those with chronic TBI.

FIG. 12 is a chart showing the fold change, 95% confidence interval, and p values between miRNA expression profiles on the PCR Array CMIHS02277 between human peripheral blood plasma obtained from subjects that have suffered acute TBI (within 24-72 hours) and those with chronic TBI.

DETAILED DESCRIPTION OF THE INVENTION

Figure 4:
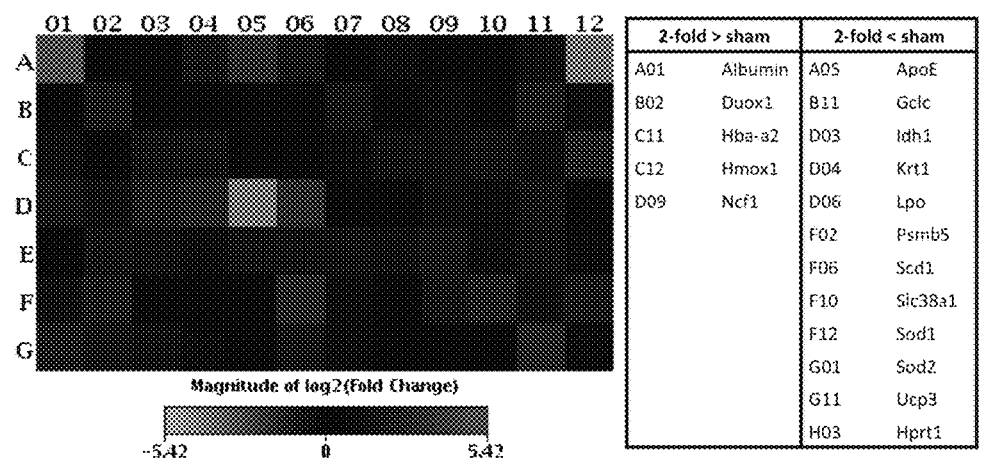
FIG. 4 is a heat map displaying fold changes in 84 oxidative stress genes comparing TBI to Sham. Total RNA was isolated from FFPE 7 μM slices from 4 sham control rats or 4 TBI rats and pooled for cDNA synthesis and preamp with universal oxidative stress array RT$^2$PCR primers. Oxidative Stress Array plates were run on a Bio-Rad iQ5 iCycler. Data for control and TBI was normalized with Rplp1. Boundary was set for 2-fold changes.

The invention features non-invasive methods of detecting, diagnosing, and tracking traumatic brain injury (TBI) or chronic traumatic encephalopathy (CTE), and related conditions, by evaluating the expression of one or more microRNAs ("miRNAs") in a sample (e.g., brain tissue, blood sample, or cerebral spinal fluid sample) derived from a subject (e.g., a human) considered to have suffered from, or is at risk of suffering from, a TBI or other neurological defect. The methods of the invention can be used to diagnose, predict, and monitor the progression of neuronal damage caused by single or multiple traumatic events, such as those experienced in, e.g., falling accidents, active sports (e.g., boxing and football), vehicular or labor accidents, or by law enforcement or military personnel. In one embodiment of the invention, the methods of the invention allow for the detection of miRNA correlated with TBI neuronal damage in the blood plasma of a subject that has or as at risk of experiencing a traumatic event.

The present invention embraces the discovery that certain miRNA species are differentially regulated following neuronal damage. Tables 1 and 2 list miRNA species (*H. sapiens* and *R. norvegicus*, respectively) found to be upregulated or downregulated in *R. norvegicus* that experience TBI in a laboratory neuronal damage model.

TABLE 1

| miRNA Name | *H. sapiens* 5' Sequence | SEQ ID NO. | *H. sapiens* 3' Sequence | SEQ ID NO. |
|---|---|---|---|---|
| miR-142 | cauaaaguagaa agcacuacu | 1 | uguaguguuucc uacuuuaugga | 37 |
| miR-21 | uagcuuaucaga cugauguuga | 2 | caacaccagucg augggcugu | 38 |
| let-7a | ugagguaguagg uuguauaguu | 3 | cuauacaaucua cugucuuuc | 39 |
| let-7b | ugagguaguagg uugugugguu | 4 | cuauacaaccua cugccuuccc | 40 |
| let-7f | ugagguaguaga uuguauaguu | 5 | | |
| miR-144 | ggauaucaucau auacuguaag | 6 | uacaguauagau gauguacu | 41 |
| miR-150 | ucucccaacccu uguaccagug | 7 | cugguacaggcc uggggacag | 42 |
| miR-32 | uauugcacauua cuaaguugca | 8 | caauuuagugug ugugauauuu | 43 |
| miR-130a | uucacauugugc uacugucugc | 9 | cagugcaauguu aaaagggcau | 44 |
| miR-101 | caguuaucacag ugcugaugcu | 10 | uacaguacugug auaacugaa | 45 |
| miR-18a | uaaggugcaucu agugcagauag | 11 | acugcccuaagu gcuccuucugg | 46 |
| let-7d | agagguaguagg uugcauaguu | 12 | cuauacgaccug cugccuuucu | 47 |

TABLE 1-continued

| miRNA Name | *H. sapiens* 5' Sequence | SEQ ID NO. | *H. sapiens* 3' Sequence | SEQ ID NO. |
|---|---|---|---|---|
| miR-181b | aacauucauugc ugucggugggu | 13 | cucacugaacaa ugaaugcaa | 48 |
| miR-223 | cguguauuugac aagcugaguu | 14 | ugucaguuuguc aaauacccca | 49 |
| miR-320 | aaaagcugggguu gagagggcga | 15 | | |
| miR-374 | uuauaauacaac cugauaagug | 16 | cuuaucagauug uauuguaauu | 50 |
| let-7e | ugagguaggagg uuguauaguu | 17 | cuauacggccuc cuagcuuucc | 51 |
| miR-196b | uaagguaguuucc uguuguuggg | 18 | ucgacagcacga cacugccuuc | 52 |
| miR-96 | uuuggcacuagc acauuuuugcu | 19 | aaucaugugcag ugccaauaug | 53 |
| miR-423 | ugaggggcagag agcgagacuuu | 20 | agcucggucuga ggccccucagu | 54 |
| miR-210 | agccccugccca ccgcacacug | 21 | cugugcguguga cagcggcuga | 55 |
| miR-182 | uuuggcaauggu agaacucacacu | 22 | ugguucuagacu ugccaacua | 56 |
| miR-196a | uagguaguuuca uguuguuggg | 23 | cggcaacaagaa acugccugag | 57 |
| miR-39-3p | | | ucaccgggugua aaucagcuug | 58 |
| miR-9 | ucuuugguuauc uagcuguauga | 24 | auaaagcuagau aaccgaaagu | 59 |
| miR-133a | agcugguaaaau ggaaccaaau | 25 | uuuggucccuu caaccagcug | 60 |
| miR-30a | uguaaacauccu cgacuggaag | 26 | cuuucagucgga uguuugcagc | 61 |
| miR-137 | uuauugcuuaag aauacgcguag | 27 | | |
| miR-23a | ggggguuccuggg gaugggauuu | 28 | aucacauugcca gggauuucc | 62 |
| miR-25 | aggcggagacuu gggcaauug | 29 | cauugcacuugu cucggucuga | 63 |
| miR-32 | uauugcacauua cuaaguugca | 30 | caauuuagugug ugugauauuu | 64 |
| miR-203a | gugaaauguuua ggaccacuag | 31 | | |
| miR-153 | ucauuuuugga uguugcagcu | 32 | uugcauagucac aaaagugauc | 65 |
| miR-218a-1 | uugugcuugauc uaaccaugu | 33 | augguuccguca agcaccaugg | 66 |
| miR-26a | uucaaguaaucc aggauaggcu | 34 | ccuauucuuggu uacuugcacg | 67 |
| miR-148a | aaaguucugaga cacuccgacu | 35 | ucagugcacuac agaacuuugu | 68 |
| miR-19a | aguuuugcauag uugcacuaca | 36 | ugugcaaaucua ugcaaaacuga | 69 |

TABLE 2

| miRNA Name | R. norvegicus 5' Sequence | SEQ ID NO. | R. norvegicus 3' Sequence | SEQ ID NO. |
|---|---|---|---|---|
| miR-142 | cauaaaguagaaagcacuacu | 70 | uguaguguuuccuacuuuaugga | 106 |
| miR-21 | uagcuuaucagacugauguuga | 71 | caacagcagucgaugggcuguc | 107 |
| let-7a | ugagguaguagguuguauaguu | 72 | cuauacaaucuacugucuuucc | 108 |
| let-7b | ugagguaguagguugugugguu | 73 | cuauacaaccuacugccuuccc | 109 |
| let-7f | ugagguaguagauuguauaguu | 74 | cuauacaaucuauugccuucc | 110 |
| miR-144 | ggauaucaucauauacuguaagu | 75 | uacaguauagaugauguacu | 111 |
| miR-150 | ucucccaaccccuuguaccagug | 76 | cuggacaggccuggggga | 112 |
| miR-32-5p | uauugcacauuacuaaguugca | 77 | gcaauuuaguguguguauauu | 113 |
| miR-130a | gcucuuuucacauugugcuacu | 78 | cagugcaauguuaaaagggcau | 114 |
| miR-101a | ucaguuaucacagugcugaugc | 79 | uacaguacuguguauaacugaa | 115 |
| miR-18a | uaaggugcaucuagugcagauag | 80 | acugcccuaagugcuccuucu | 116 |
| let-7d | agagguaguagguugcauaguu | 81 | cuauacgaccugcugccuuucu | 117 |
| miR-181b | aacauucauugcugucggugggu | 82 | cucacugaacaaugaaugcaa | 118 |
| miR-223 | cguguauuugacaagcugaguug | 83 | ugucaguuugucaaauaccc | 119 |
| miR-320 | gccuucucuucccgguucuucc | 84 | aaaagcugggugagagggcga | 120 |
| miR-374 | auauaauacaaccugcuaagug | 85 | cuuagcacguuguauuauuauu | 121 |
| let-7e | ugagguaggagguuguauaguu | 86 | cuauacgccuccuagcuuucc | 122 |
| miR-196b | uagguaguuuccuguuguuggg | 87 | ucgacagcacgacacugccuuca | 123 |
| miR-96 | uuuggcacuagcacauuuugcu | 88 | caaucaugugagugccaauau | 124 |
| miR-423 | ugaggggcagagagcgagacuuuu | 89 | agcucggucgaggccccucagu | 125 |
| miR-210 | agccacugcccacagcacacug | 90 | cugugcgugugacagcggcuga | 126 |
| miR-182 | uuuggcaauggugaacucacaccg | 91 | | |
| miR-196a | uagguaguuucauguuguuggg | 92 | ucggcaacaagaaacugccuga | 127 |
| miR-39 | | | | |
| miR-9a | ucuuugguuaucuagcuguauga | 93 | auaaagcuagauaaccgaaagu | 128 |
| miR-133a | agcugguaaaauggaaccaaau | 94 | uuuggucccccuucaaccagcug | 129 |
| miR-30a | uguaaacauccucgacuggaag | 95 | cuuucagucggauguuugcagc | 130 |
| miR-137 | acgguauucuugggggauaa | 96 | uuauugcuuaagaauacgcuag | 131 |
| miR-23a | gggguuccuggggauggauuu | 97 | aucacauugccagggauuucc | 132 |
| miR-25 | aggcggagacacgggcaauugc | 98 | cauugcacuugucucggucuga | 133 |
| miR-32 | uauugcacauuacuaaguugca | 99 | gcaauuuaguguguguauauu | 134 |
| miR-203a | agugguucuuaacaguucaac | 100 | gugaaauguuaaggaccacuag | 135 |
| miR-153 | gucauuuuuguagauuugcagcu | 101 | uugcauagucacaaaagugauc | 136 |
| miR-218a-1 | uugugcuugaucuaaccaugu | 102 | aaacaugguuccgucaagcac | 137 |
| miR-26a | uucaaguaauccaggauaggcu | 103 | ccuauucuugguuacuugcac | 138 |
| miR-148 | gaaguucuguuauacacucagg | 104 | ucagugcaucacagaacuuugu | 139 |
| miR-19a | ucguuuugcauaguugcacu | 105 | ugugcaaaucuaugcaaaacuga | 140 |

Methods of miRNA Expression Profiling

The expression level of at least one miRNA species can be measured in a biological sample (e.g., an organ, tissue, or cell sample, such as brain tissue, blood sample, or cerebral spinal fluid (CSF)) obtained from a patient (e.g., a human). For example, a tissue sample (e.g., brain tissue, blood, or CSF) can be removed from a patient suspected of suffering from or at risk of suffering a brain injury (e.g., TBI or CTE) by conventional biopsy techniques. In another embodiment, a blood or CSF sample can be removed from the patient (e.g., a human), and cells (e.g., white blood cells) or serum can be isolated for RNA extraction by standard techniques. In order to determine baseline miRNA expression profiles, a blood, CSF, or tissue sample is preferably obtained from the patient prior to initiation of any activity that carries a heightened risk of TBI, including but not limited to impact sports (e.g., boxing, American football, rugby, hockey, baseball, and soccer), military or law enforcement service, medical conditions that leave subjects susceptible to falls (e.g., blindness, advanced age), or any other that places the subject at increased risk of suffering TBI (e.g., race car driving, skydiving, and victims of assault). Baseline blood or tissue samples are also ideally obtained prior to radiotherapy, chemotherapy or other therapeutic treatment in order to gauge miRNA expression profile changes during the course of treatment. A corresponding control tissue or blood sample can be obtained from unaffected tissues of the patient, from a normal human individual or population of normal individuals, or from cultured cells corresponding to the majority of cells in the patient's sample. The control tissue or blood sample is then processed along with the sample from the patient, so that the miRNA expression profile derived from the patient's sample can be compared to a corresponding miRNA expression profile derived from a sample taken from a control subject or group. A reference miRNA expression profile standard for the biological sample can also be used as a control.

An alteration (e.g., an increase or decrease) in the level of one or more of the miRNAs identified herein (e.g., SEQ ID NOS:1-140) in the sample obtained from a patient (e.g., a human), relative to the level of corresponding miRNAs in a control sample, is indicative of the presence of brain injury (e.g., TBI) in the patient. In one embodiment, the expression level of at least one miRNA in the test sample is greater than the expression level of a corresponding miRNA in the control sample (i.e., expression of the miRNA is "up-regulated"). As used herein, expression of a miRNA is "up-regulated" when the amount of miRNA in a fluid, cell, or tissue sample from a patient is greater than the amount of the same miRNA in a control fluid, cell, or tissue sample. In another embodiment, the expression level of the at least one miRNA in the test sample is less than the expression level of the corresponding miRNA in the control sample (i.e., expression of the miRNA is "down-regulated"). As used herein, expression of a miRNA is "down-regulated" when the amount of miRNA produced in a fluid, cell, or tissue sample from a patient is less than the amount produced in a fluid, control cell, or tissue sample. A patient miRNA expression profile is considered to indicate the presence of a brain injury if the up or down-regulation is 1.2, 1.3, 1.4, 1.5, 1.6, 1.7, 1.8, 1.9, or 2.0 fold or greater relative to the control expression profile. The relative miRNA expression in the control and normal samples can be determined with respect to one or more miRNA expression standards. The standards can comprise, for example, a zero miRNA gene expression level, the miRNA expression profiles of standardized cell lines, the miRNA expression profiles in unaffected tissues of the patient (e.g., a human), or the average level of miRNA expression previously obtained for a population of normal controls (e.g., human controls).

The level of a miRNA expression in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miRNA species is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, e.g., Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes for Northern blot hybridization of a given miRNA can be produced from the nucleic acid sequences of the miRNA sequences described and listed herein and include, but are not limited to, probes having at least about 70%, 75%, 80%, 85%, 90%, 95%, 98%, 99% or complete complementarity to a miRNA of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference. For example, the nucleic acid probe can be labeled with, e.g., a radionuclide, such as $^{3}H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), J. Mol. Biol. 113:237-251 or by the random priming method of Fienberg et al. (1983), Anal. Biochem. 132:6-13, the entire disclosures of which are incorporated herein by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miRNA can be produced from the nucleic acid sequences having at least about 70%, 75%, 80%, 85%, 90%, 95%, 98%, 99% or complete complementarity to a miRNA of interest, as described above.

The relative number of miRNA gene transcripts in cells can also be determined by reverse transcription of miRNA gene transcripts, followed by amplification of the reverse-transcribed transcripts by polymerase chain reaction (RT-PCR). The levels of miRNA gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miRNA species in a sample (e.g., brain tissue, blood, or cerebral spinal fluid (CSF)). In other instances, it may be desirable to determine the expression level of the transcripts of all known miRNA species correlated with a brain injury. Assessing brain injury-specific expression levels for hundreds of miRNA species is time consuming and requires a large amount of total RNA (e.g., at least 20 micrograms for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotides) probes that are specific for a set of miRNA species. Using such a microarray, the expression level of multiple microRNAs in a biological sample (e.g., brain tissue, blood, or cerebral spinal fluid (CSF)) can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level consistent with a suspected disease, condition, or disorder, such as traumatic brain injury.

Accordingly, the invention provides methods of diagnosing whether a subject has, or is at increased risk of suffering from a TBI comprising reverse transcribing RNA from a test sample (e.g., brain tissue, blood, or cerebral spinal fluid (CSF)) obtained from the subject (e.g., a human) to provide a set of target oligodeoxynucleotides, hybridizing the target oligodeoxynucleotides to a microarray comprising miRNA-specific probe oligonucleotides to provide a hybridization profile for the test sample, and comparing the test sample hybridization profile to a hybridization profile generated from a control sample or reference standard, wherein an alteration in the signal of at least one miRNA is indicative of the subject either having, or being at risk for developing, TBI. In one embodiment, the microarray comprises miRNA-specific probe oligonucleotides for a substantial portion of all known human miRNAs. In one embodiment, the microarray comprises miRNA-specific probe oligonucleotides for one or more miRNAs selected from the group consisting of miR-142, miR-21, let-7a, let-7b, let-7f, miR-144, miR-150, miR-32, miR-130a, miR-101a, miR-18a, let-7d, miR-181b, miR-223, miR-320, miR-374, let-7e, miR-196b, miR-96, miR-423, miR-210, miR-182, miR-196a, miR-39, miR-9a, miR-133a, miR-30a, miR-137, miR-23a, miR-25, miR-32, miR-203a, miR-153, miR-218-1, miR-26a, miR-148a, and miR-19a.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs or other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT (Tris HCl/NaCl/Tween 20) at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRNAs, in the patient sample. Image intensities of each spot on the array are proportional to the abundance of the corresponding miRNA in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 micrograms of total RNA. The relatively limited number of miRNAs (a few hundred per species) allows the construction of a common microarray for several species, with distinct oligonucleotide probes for each. Such a tool would allow for analysis of trans-species expression for each known miRNA under various conditions.

In addition to use for quantitative expression level assays of specific miRNA, a microchip containing miRNA-specific probe oligonucleotides corresponding to a substantial portion of the miRNome, preferably the entire miRNome, may be employed to carry out miRNA gene expression profiling, for analysis of miRNA expression patterns. Distinct miRNA signatures can be associated with established disease markers, or directly with a disease state.

According to the expression profiling methods described herein, total RNA from a sample (e.g., brain tissue, blood, or cerebral spinal fluid (CSF)) from a subject (e.g., a human) suspected of suffering or at risk of suffering a TBI is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile derived from a normal, i.e., non-TBI, control sample. An alteration in the signal is indicative of the presence of, or propensity to develop, TBI in the subject.

Other techniques for measuring miRNA gene expression are also within the skill in the art, and include various techniques for measuring rates of RNA transcription and degradation.

Treatment of Brain Injury

As described herein, brain injury is associated with marked loss of System $x_c^-$ antiporter expression in brain tissues and an overall loss in antioxidant capacity in these tissues. Weak antioxidant mechanisms allow for accumulation of reactive oxygen species (ROS) that chemically damage surround cells and tissues.

Upon making a clinical determination that a patient (e.g., a human) has suffered a brain injury, a clinician may determine that administration of an antioxidant or antioxidant therapy course is appropriate. Examples of antioxidants include, but are not limited to, alpha-tocopherol, ascorbate, coenzyme Q, alpha-lipoic acid, curcumin, glutathione, uric acid, carotenes (e.g., retinol, beta-carotene), superoxide dismutase, catalases, peroxiredoxins, thioredoxins, tirilazad mesylate, and NXY-059. In one embodiment, the patient is administered a therapeutically-effective amount of one or more antioxidants in order to slow the progression of brain injury.

Methods of Diagnostic Imaging

The present invention provides for the diagnosis and medical evaluation of patients (e.g., a human) suffering from, or at risk of suffering from TBI, CTE, or related conditions. For example, an imaging agent specific for System $x_c^-$ can also be used, alone or in combination with other agents and compounds, in medical imaging applications to diagnose or follow the progression of diseases, disorders, conditions or symptoms related to TBI or CTE in a patient (e.g., a human). For example, radiologists and other medical clinicians are skilled in the use of radiographic imaging devices, such as positron emission tomography (PET) scanners, and methods of imaging tracer compounds, such as the radionuclides. (e.g., Saha, Basics of PET Imaging: Physics, Chemistry, and Regulations, Springer (2010) ISBN 978-1-4419-0804-9, hereby incorporated by reference).

The methods of the present invention are also useful for the medical imaging and diagnosis of humans and animals, e.g., domesticated animal, companion animals (e.g., dogs and cats), exotic animals, farm animals (e.g., ungulates, including horses, cows, sheep, goats, and pigs), and animals used in scientific research (e.g., rodents and non-human primates).

Compound Administration and Formulation

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid. A compound can be prepared in a form of pharmaceutically acceptable salts that will be prepared from nontoxic inorganic or organic bases including but not limited to aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally-occurring substituted amines, cyclic amines, and basic ion exchange resins, such as arginine, betaine, caffeine, choline, ethylamine, 2-diethylaminoethano, 1,2-dimethylaminoethanol, ethanolamine, ethylenediamine, N-ethyl-morpholine, N-ethylpiperidine, glucamine, glucosamine, histidine, hydroxylamine, isopropylamine, lysine, methylglucamine, morpholine, piperazine, piperidine, polyamine resins, procaine, purines, theobromine, triethylamine, trimethylamine, trishydroxylmethyl amino methane, tripropyl amine, and tromethamine.

If the compounds are basic, salts could be prepared in a form of pharmaceutically acceptable salts that will be prepared from nontoxic inorganic or organic acids including but not limited to hydrochloric, hydrobromic, phosphoric, sulfuric, tartaric, citric, acetic, fumaric, alkyl sulphonic, naphthalenesulphonic, para-toluenesulphonic, camphoric acids, benzenesulfonic, benzoic, camphorsulfonic, citric, ethanesulfonic, gluconic, glutamic, isethonic, lactic, maleic, malic, mandelic, methanesulfonic, mucic, nitric, pamoic, pantothenic, phosphoric, and succinic.

While it may be possible for the compounds to be administered as the raw chemical, it is also possible to present them as a pharmaceutical formulation. Accordingly, the present invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. When used in the diagnostic imaging methods of the invention, compounds can be administered to the patient (e.g., a human) by intravenous injection. The formulations may conveniently be presented in unit dosage form and may be prepared by any of the methods well known in the art of pharmacy. All methods include the step of bringing into association a compound of the present invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Compounds may be formulated for parenteral administration by injection, e.g., by bolus injection or continuous infusion. Formulations for injection may be presented in unit dosage form, e.g., in ampoules or in multi-dose containers, with an added preservative. Compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, a compound may also be formulated as a depot preparation. Such long acting formulations may be administered by implantation (for example subcutaneously or intramuscularly) or by intramuscular injection. Thus, for example, a compound may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, a compound may take the form of tablets, lozenges, pastilles, or gels formulated in conventional manner. Such compositions may comprise the active ingredient in a flavored basis such as sucrose and acacia or tragacanth.

A compound may also be formulated in rectal compositions such as suppositories or retention enemas, e.g., containing conventional suppository bases such as cocoa butter, polyethylene glycol, or other glycerides.

A compound may be administered topically, that is by non-systemic administration. This includes the application of a compound externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include solid, liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Via the topical route, a pharmaceutical composition may be in the form of liquid or semi liquid such as ointments, or in the form of solid such as powders. It may also be in the form of suspensions such as polymeric microspheres, or polymer patches and hydrogels allowing a controlled release. This topical composition may be in anhydrous form, in aqueous form or in the form of an emulsion. The compounds are used topically at a concentration generally of between 0.001% and 10% by weight and preferably between 0.01% and 1% by weight, relative to the total weight of the composition.

For administration by inhalation, a compound can be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, a compound may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, formulations described herein may include other agents conventional in the art having regard to the type of formulation in question, for example those suitable for oral administration may include flavoring agents.

A compound may be administered orally or via injection at a dose of from 0.1 to 500 mg/kg per day. The dose range for adult humans is generally from 5 mg to 2 g/day. Tablets or other forms of presentation provided in discrete units may conveniently contain an amount of compound which is effective at such dosage or as a multiple of the same, for instance, units containing 5 mg to 500 mg, usually around 10 mg to 200 mg.

Compounds can be administered at a daily dose of about 0.001 mg/kg to 100 mg/kg of body weight, in 1 to 3 dosage intakes. Further, compounds can be used systemically, at a concentration generally of between 0.001% and 10% by weight and preferably between 0.01% and 1% by weight, relative to the weight of the composition.

The amount of active ingredient that may be combined with the carrier materials to produce a single dosage form will vary depending upon the host treated and the particular mode of administration.

A compound can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one compound described herein (or a pharmaceutically acceptable salt, ester, or prodrug thereof) in combination with another therapeutic or diagnostic agent. By way of example only, if one of the side effects experienced by a patient upon receiving one of the compounds described herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for pain involving administration of one of the compounds described herein, increased therapeutic benefit may result by also providing the patient with another therapeutic agent for pain. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of a compound together with inert or active compounds, or other drugs including wetting agents, flavor enhancers, preserving agents, stabilizers, humidity regulators, pH regulators, osmotic pressure modifiers, emulsifiers, UV-A and UV-B screening agents, antioxidants, depigmenting agents such as hydroquinone or kojic acid, emollients, moisturizers, for instance glycerol, PEG 400, or urea, antiseborrhoeic or antiacne agents, such as S-carboxymethylcysteine, S-benzylcysteamine, salts thereof or derivatives thereof, or benzoyl peroxide, antibiotics, for instance erythromycin and tetracyclines, chemotherapeutic agent, for example, paclitaxel, antifungal agents such as ketoconazole, agents for promoting regrowth of the hair, for example, minoxidil (2,4-diamino-6-piperidinopyrimidine 3-oxide), non-steroidal anti-inflammatory agents, carotenoids, and especially p-carotene, antpsoriatic agents such as anthralin and its derivatives, eicosa-5,8,11,14-tetraynoic acid and eicosa-5,8,11-triynoic acid, and esters and amides thereof, retinoids, e.g., RAR or RXR receptor ligands, which may be natural or synthetic, corticosteroids or oestrogens, alpha-hydroxy acids and a-keto acids or derivatives thereof, such as lactic acid, malic acid, citric acid, and also the salts, amides or esters thereof, or p-hydroxy acids or derivatives thereof, such as salicylic acid and the salts, amides or esters thereof, ion-channel blockers such as potassium-channel blockers, or alternatively, more particularly for the pharmaceutical compositions, in combination with medicaments known to interfere with the immune system, anticonvulsant agents include, and are not limited to, topiramate, analogs of topiramate, carbamazepine, valproic acid, lamotrigine, gabapentin, phenytoin and the like and mixtures or pharmaceutically acceptable salts thereof. A person skilled in the art will take care to select the other compound(s) to be added to these compositions such that the advantageous properties intrinsically associated with the compounds are not, or are not substantially, adversely affected by the envisaged addition.

In any case, the multiple therapeutic or diagnostic agents may be administered in any order or even simultaneously. If simultaneously, the multiple therapeutic or diagnostic agents may be provided in a single, unified form, or in multiple forms (by way of example only, either as a single pill or as two separate pills). One of the therapeutic or diagnostic agents may be given in multiple doses, or both may be given as multiple doses. If not simultaneous, the timing between the multiple doses may be any duration of time ranging from a few minutes to four weeks.

Thus, in another aspect, methods for diagnosing or treating diseases, disorders, conditions, or symptoms in a subject (e.g., a human or animal) in need of such treatment are presented herein, the methods comprising the step of administering to the subject an amount of a compound effective to reduce or prevent the disease, disorder, condition, or symptom, in combination with at least one additional agent for the treatment of said disorder that is known in the art.

EXAMPLES

It is understood that the foregoing examples are merely illustrative of the present invention. Certain modifications of the articles and/or methods employed may be made and still achieve the objectives of the invention. Such modifications are contemplated as within the scope of the claimed invention.

Example 1. Gene Array Analysis Before and after TBI in Rodent Model

System $x_c^-$ is a cysteine/glutamate antiporter comprised of two distinct subunits xCT and 4F2hc (SLC3A2) and a member of the heteromeric amino acid transporter (HAT) family. Under physiological conditions, System $x_c^-$ mediates the exchange of extracellular L-cysteine and intracellular L-glutamate across the plasma membrane. In the CNS, the influx of L-cysteine represents the critical rate limiting step in the biosynthesis of glutathione (GSH) while the concurrent efflux of L-glutamate serve as a non-vesicular route of excitatory neurotransmitter release to initiate excitatory amino acid (EAA) signalling. GSH serves as the key cellular antioxidant responsible for scavenging reactive oxygen species (ROS) that develop as a result of physiological cellular metabolism. Thus a global loss of System $x_c^-$ activity would result in decreased intracellular glutathione levels, leaving the CNS vulnerable to oxidative stress due to an increase in cellular ROS. While it is likely that other antioxidant systems such as SOD1, SOD2, and catalase would initially metabolize ROS, as an individual ages these compenstatory enzymes lose scavenging efficiency resulting in a prolonged elevation in ROS. With glutathione missing and supporting antioxidant systems operating with less efficiency, ROS accumulation could result in unsurmountable oxidative stress leading to neuropathology associated with the gradual process of neurodegenerative events leading to CTE.

In animal studies we have found that a single TBI produced a rapid, global, long-term loss of a key transporter protein subunit, xCT (SLC7A11; FIGS. 1-3). Over time (46 days post-TBI), the levels of xCT gradually returned but never reached pre-TBI levels suggesting the injury induced a long-term loss of xCT. xCT is the catalytic subunit of System xc–, a ubiquitous antiporter responsible for the biosynthesis of gluthathione (GSH) in the brain. GSH is the primary cellular anti-oxidant that scavenges damaging reactive oxygen species (ROS) that develop as a result of normal metabolism or neuronal injury.

Figure 5:
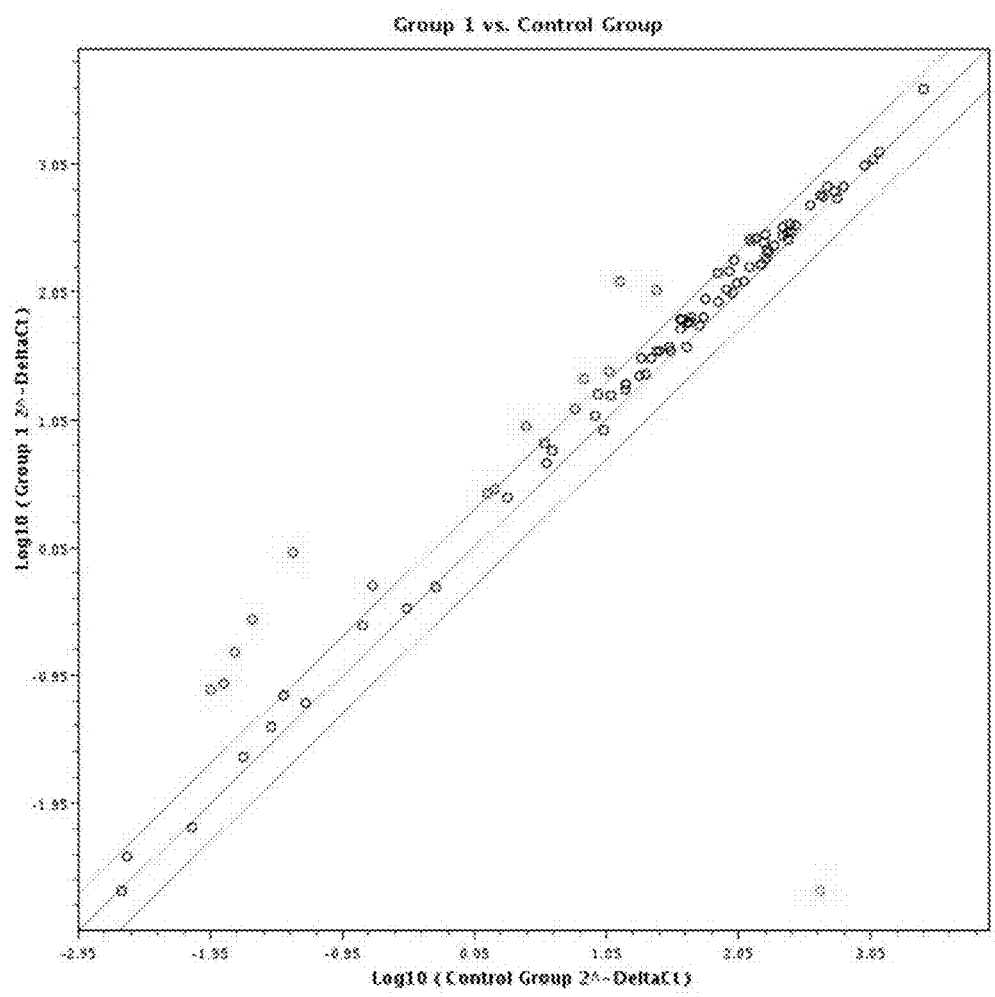
FIG. 5 is a scatter plot displaying fold changes in predicted xCT targeting miRNA. Total RNA was isolated from FFPE 7 μM slices from 4 sham control rats or 4 TBI rats and pooled for cDNA synthesis and preamp with universal oxidative stress array RT$^2$PCR primers. Rat miFinder Array plates were run on a Bio-Rad iQ5 iCycler. Data for control and TBI was normalized with SNORD61 and SNORD95. Boundary was set for 2-fold changes.

Example 2: miRNA Expression Profiles of Oxidative Stress and Antioxidant Defense Genes To follow up this study, we performed a gene array analysis to determine if oxidative stress genes up-regulate to compensate for the loss of GSH (FIG. 4). From this study we found exactly the opposite occurred; TBI resulted in a down-regulation of key anti-oxidant defense genes leaving neurons critically susceptible to ROS damage. In an effort to elucidate the mechanism of how the xCT subunit and anti-oxidant defense genes were down-regulated by TBI we performed a microRNA (miRNA) expression profile study on rat (*R. norvegus*) cortical brain tissue following neuronal injury in a lateral fluid percussion TBI model (FIG. 5). In light of our prior findings, we chose miRNAs that specifically interact with anti-oxidant defense genes and xCT. A specific cluster of miRNAs that were significantly (2-13 fold) up or down regulated as a result of TBI was discovered (Table 3). Further studies indicate all of these highly conserved miRNAs are novel to TBI research, and can be detected in the plasma.

TABLE 3

| miRNA Name | Fold Up-Regulation |
|---|---|
| rno-miR-142-3p | 2.0894 |
| rno-miR-21-5p | 1.7652 |
| rno-let-7a-5p | 1.7782 |
| rno-let-7b-5p | 1.6374 |
| rno-let-7f-5p | 3.9548 |
| rno-miR-144-3p | 20.49 |
| rno-miR-150-5p | 8.8712 |
| rno-miR-32-5p | 1.9359 |
| rno-miR-130a-3p | 1.5581 |
| rno-miR-101a-3p | 1.8134 |
| rno-miR-18a-5p | 1.8539 |
| rno-let-7d-5p | 1.8442 |
| rno-miR-181b-5p | 1.5577 |
| rno-miR-223-3p | 3.3426 |
| rno-miR-320-3p | 1.6849 |
| rno-miR-374-5p | 1.8993 |
| rno-let-7e-5p | 1.9764 |
| rno-miR-196b-5p | 8.9494 |
| rno-miR-96-5p | 1.6113 |
| rno-miR-423-3p | 2.8863 |
| rno-miR-210-3p | 1.7867 |
| rno-miR-182 | 2.7308 |
| rno-miR-196a-5p | 12.2571 |
| cel-miR-39-3p | 6.3604 |
| cel-miR-39-3p | 6.9183 |
| Fold Down-Regulation | |
| rno-miR-9a-5p | −220228.6761 |

Example 3: miRNA Expression Profiles of Human Peripheral Blood Plasma

Approximately 3 mL of blood was collected from each subject and processed as described below. Total RNA was isolated and prepared from 200 μL plasma according to the miRNeasy Serum/Plasma Kit (50) protocol according to the manufacturer's instructions (Qiagen). cDNA was prepared using the isolated total RNA. Real-time PCR was performed using the Qiagen miScript SYBR Green PCR kit and custom miScript miRNA PCR Array on a Bio-Rasd iQ5 cycler. Data analysis was performed using the Qiagen Data Analysis Center. The following plasma samples were obtained:

| Sample Source | Description | n = |
|---|---|---|
| Control | No TBI, non-athlete | 14 |
| Football Players | No TBI with 3 months | 49 |
| Soccer Players | No TBI with 3 months | 19 |
| Acute TBI | 24-72 post-TBI | 4 |
| Chronic TBI | 3 months post-TBI | 6 |

All plasma samples were obtained by voluntary donation according to the Institutional Review Board protocols of The University of Montana. Samples were obtained at random (control group), from student athletes participating in football or soccer sports, and from subjects known to have suffered acute (within 72 hours) TBI or chronic (greater than 72 hours) TBI.

The data presented shows the fold change when comparing sample, the 95% CI and p values. Initial analysis of the data show that there are strong trends towards increases in some miRNA levels following Acute TBI with miR-142-3p, miR-150-5p, and miR-196b-5p showing significance in the screening between Control and Acute TBI. Significant differences were also found in let-7f-5p, miR-150-5p, and miR-196b-5p between Control and Soccer Players. Much of the data is trending toward significance (i.e., $p<0.05$). The data also suggest there may be a strong influence of gender on the changes in miRNA levels (Football v Soccer Players). Interestingly the analysis of the chronic TBI group suggests that the levels of miRNA rebound and drop potentially as a compensatory measure and this finding suggests we may able to further use this panel to distinguish between acute and chronic TBI using this panel.

All Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Other embodiments are within the claims.

What is claimed is:

1. A method of detecting a traumatic brain injury in a patient comprising the steps of
    contacting a biological sample derived from a patient with at least one miR-specific oligodeoxynucleotide probe having at least 70% complementarity to a sequence selected from SEQ ID NOs. 5, 30, 41 and 54;
    measuring the expression level of at least one microRNA represented by a sequence selected from SEQ ID NOs. 5, 30, 41 and 54 in said patient by quantifying said at least one miR-specific oligodeoxynucleotide probe in said biological sample obtained from said patient;
    obtaining or performing a measurement of a control expression level of said at least one microRNA represented by a sequence selected from SEQ ID NOs. 5, 30, 41 and 54 in a control biological sample derived from a healthy subject or tissue;
    measuring a 1.2 fold or greater increase in the expression level of said at least one microRNA represented by a sequence selected from SEQ ID NOs. 5, 30, 41 and 54 in said patient compared with said control expression level derived from said healthy subject or tissue, to thereby determine that said patient has suffered a traumatic brain injury; and
    treating said traumatic brain injury in said patient determined to have suffered a traumatic brain injury.

2. The method of claim 1 wherein said treating said patient determined to have suffered a traumatic brain injury comprises administering to said patient a therapeutically-effective amount of an antioxidant.

3. The method of claim 2, wherein said antioxidant is selected from the group consisting of alpha-tocopherol, ascorbate, coenzyme Q, alpha-lipoic acid, curcumin, glutathione, uric acid, a carotene, superoxide dismutase, a catalase, a peroxiredoxin, a thioredoxin, tirilazad mesylate, and NXY-059.

4. The method of claim 1, wherein said patient is a human.

5. The method of claim 1, wherein said biological sample is blood, cerebral spinal fluid, saliva, or brain tissue.

6. The method of claim 1, wherein said biological sample is blood plasma or serum.

7. The method of claim 1, wherein said measuring comprises polymerase chain reaction (PCR), in situ hybridization, Northern blot, or gene chip analysis.

8. The method of claim 1, wherein said miR-specific oligodeoxynucleotide probe comprises DNA.

9. The method of claim 1, wherein said microRNA control expression level is derived from a sample derived from said patient prior to sustaining said traumatic brain injury.

10. The method of claim 1, wherein said biological sample is derived from said patient within seventy-two (72) hours of sustaining said traumatic brain injury.

11. The method of claim 1 repeated on biological samples derived from said patient over a period of time, wherein changes in said measured microRNA expression levels in said patient over time indicate progression or regression of said traumatic brain injury in said patient.

12. The method of claim 1, wherein said at least one miR-specific oligodeoxynucleotide probe has at least 90% complementarity to a sequence selected from SEQ ID NOs. 5, 30, 41 and 54.

13. A minimally-invasive method of detecting a traumatic brain injury in a patient comprising the steps of
    contacting a blood, plasma, or serum sample derived from a patient with at least one miR-specific oligodeoxynucleotide probe having at least 70% complementarity to a sequence selected from SEQ ID NOs. 5, 30, 41 and 54;
    measuring the expression level of at least one microRNA represented by a sequence selected from SEQ ID NOs. 5, 30, 41 and 54 by quantifying said at least one miR-specific oligodeoxynucleotide probe in said sample derived from said patient;
    obtaining or performing a measurement of a control expression level of said at least one microRNA represented by a sequence selected from SEQ ID NOs. 5, 30, 41 and 54 in a control blood, plasma, or serum sample derived from a healthy subject or tissue;
    measuring a 1.2 fold or greater increase in the expression level of said at least one microRNA represented by a sequence selected from SEQ ID NOs. 5, 30, 41 and 54 in said patient compared with said control expression level derived from said healthy subject or tissue, to thereby determine that said patient has suffered a traumatic brain injury; and
    treating said traumatic brain injury in said patient determined to have suffered a traumatic brain injury.

14. The method of claim 1, comprising
    contacting a control biological sample obtained from a healthy subject or tissue with at least one miR-specific oligodeoxynucleotide probe having at least 70% complementarity to a sequence selected from SEQ ID NOs. 5, 30, 41 and 54; and
    measuring the expression level of said at least one microRNA represented by SEQ ID NOs. 5, 30, 41 and 54 in the healthy subject or tissue by quantifying said at least one miR-specific oligodeoxynucleotide probe in said control biological sample, to thereby obtain a measurement of a control expression level of said at least one microRNA represented by a sequence selected from SEQ ID NOs. 5, 30, 41 and 54.

15. The method of claim 1, wherein the patient is suspected of suffering from or is at risk of suffering from a traumatic brain injury.

16. The method of claim 1, wherein the control biological sample is derived from one or more healthy subjects or from one or more healthy tissue(s) of said patient not affected by traumatic brain injury.

17. The method of claim 1, wherein said healthy subject is not suffering or suspected of suffering from a traumatic brain injury and/or not having previously suffered from a traumatic brain injury.

* * * * *

SEQUENCE LISTING

```
<160> NUMBER OF SEQ ID NOS: 140

<210> SEQ ID NO 1
<211> LENGTH: 21
<212> TYPE: DNA
<213> ORGANISM: Homo sapiens

<400> SEQUENCE: 1
cauaaaguag aaagcacuac u                                                   21

<210> SEQ ID NO 2
<211> LENGTH: 22
<212> TYPE: DNA
<213> ORGANISM: Homo sapiens

<400> SEQUENCE: 2
uagcuuauca gacugauguu ga                                                  22

<210> SEQ ID NO 3
<211> LENGTH: 22
<212> TYPE: DNA
<213> ORGANISM: Homo sapiens

<400> SEQUENCE: 3
ugagguagua gguuguauag uu                                                  22

<210> SEQ ID NO 4
<211> LENGTH: 22
<212> TYPE: DNA
<213> ORGANISM: Homo sapiens

<400> SEQUENCE: 4
ugagguagua gguugugugg uu                                                  22

<210> SEQ ID NO 5
<211> LENGTH: 22
<212> TYPE: DNA
<213> ORGANISM: Homo sapiens

<400> SEQUENCE: 5
ugagguagua gauuguauag uu                                                  22

<210> SEQ ID NO 6
<211> LENGTH: 22
<212> TYPE: DNA
<213> ORGANISM: Homo sapiens

<400> SEQUENCE: 6
ggauaucauc auauacugua ag                                                  22
```

```
<210> SEQ ID NO 7
<211> LENGTH: 22
<212> TYPE: DNA
<213> ORGANISM: Homo sapiens

<400> SEQUENCE: 7
ucucccaacc cuuguaccag ug                                              22

<210> SEQ ID NO 8
<211> LENGTH: 22
<212> TYPE: DNA
<213> ORGANISM: Homo sapiens

<400> SEQUENCE: 8
uauugcacau uacuaaguug ca                                              22

<210> SEQ ID NO 9
<211> LENGTH: 22
<212> TYPE: DNA
<213> ORGANISM: Homo sapiens

<400> SEQUENCE: 9
uucacauugu gcuacugucu gc                                              22

<210> SEQ ID NO 10
<211> LENGTH: 22
<212> TYPE: DNA
<213> ORGANISM: Homo sapiens

<400> SEQUENCE: 10
caguuaucac agugcugaug cu                                              22

<210> SEQ ID NO 11
<211> LENGTH: 23
<212> TYPE: DNA
<213> ORGANISM: Homo sapiens

<400> SEQUENCE: 11
uaaggugcau cuagugcaga uag                                             23

<210> SEQ ID NO 12
<211> LENGTH: 22
<212> TYPE: DNA
<213> ORGANISM: Homo sapiens

<400> SEQUENCE: 12
agagguagua gguugcauag uu                                              22

<210> SEQ ID NO 13
<211> LENGTH: 23
<212> TYPE: DNA
<213> ORGANISM: Homo sapiens

<400> SEQUENCE: 13
aacauucauu gcugucggug ggu                                             23

<210> SEQ ID NO 14
<211> LENGTH: 22
<212> TYPE: DNA
<213> ORGANISM: Homo sapiens

<400> SEQUENCE: 14
cguguauuug acaagcugag uu                                              22
```

```
<210> SEQ ID NO 15
<211> LENGTH: 22
<212> TYPE: DNA
<213> ORGANISM: Homo sapiens

<400> SEQUENCE: 15
aaaagcuggg uugagagggc ga                                          22

<210> SEQ ID NO 16
<211> LENGTH: 22
<212> TYPE: DNA
<213> ORGANISM: Homo sapiens

<400> SEQUENCE: 16
uuauaauaca accugauaag ug                                          22

<210> SEQ ID NO 17
<211> LENGTH: 22
<212> TYPE: DNA
<213> ORGANISM: Homo sapiens

<400> SEQUENCE: 17
ugagguagga gguuguauag uu                                          22

<210> SEQ ID NO 18
<211> LENGTH: 22
<212> TYPE: DNA
<213> ORGANISM: Homo sapiens

<400> SEQUENCE: 18
uagguaguuu ccuguuguug gg                                          22

<210> SEQ ID NO 19
<211> LENGTH: 23
<212> TYPE: DNA
<213> ORGANISM: Homo sapiens

<400> SEQUENCE: 19
uuuggcacua gcacauuuuu gcu                                         23

<210> SEQ ID NO 20
<211> LENGTH: 23
<212> TYPE: DNA
<213> ORGANISM: Homo sapiens

<400> SEQUENCE: 20 ugagggcag agagcgagac uuu                                          23

<210> SEQ ID NO 21
<211> LENGTH: 22
<212> TYPE: DNA
<213> ORGANISM: Homo sapiens

<400> SEQUENCE: 21
agccccugcc caccgcacac ug                                          22

<210> SEQ ID NO 22
<211> LENGTH: 24
<212> TYPE: DNA
<213> ORGANISM: Homo sapiens

<400> SEQUENCE: 22
uuuggcaaug guagaacuca cacu                                        24
```

-continued

<210> SEQ ID NO 23
<211> LENGTH: 22
<212> TYPE: DNA
<213> ORGANISM: Homo sapiens

<400> SEQUENCE: 23
uagguaguuu cauguuguug gg 22

<210> SEQ ID NO 24
<211> LENGTH: 23
<212> TYPE: DNA
<213> ORGANISM: Homo sapiens

<400> SEQUENCE: 24
ucuuugguua ucuagcugua uga 23

<210> SEQ ID NO 25
<211> LENGTH: 22
<212> TYPE: DNA
<213> ORGANISM: Homo sapiens

<400> SEQUENCE: 25
agcugguaaa auggaaccaa au 22

<210> SEQ ID NO 26
<211> LENGTH: 22
<212> TYPE: DNA
<213> ORGANISM: Homo sapiens

<400> SEQUENCE: 26
uguaaacauc cucgacugga ag 22

<210> SEQ ID NO 27
<211> LENGTH: 23
<212> TYPE: DNA
<213> ORGANISM: Homo sapiens

<400> SEQUENCE: 27
uuauugcuua agaauacgcg uag 23

<210> SEQ ID NO 28
<211> LENGTH: 22
<212> TYPE: DNA
<213> ORGANISM: Homo sapiens

<400> SEQUENCE: 28
gggguuccug gggaugggau uu 22

<210> SEQ ID NO 29
<211> LENGTH: 21
<212> TYPE: DNA
<213> ORGANISM: Homo sapiens

<400> SEQUENCE: 29
aggcggagac uugggcaauu g 21

<210> SEQ ID NO 30
<211> LENGTH: 22
<212> TYPE: DNA
<213> ORGANISM: Homo sapiens

<400> SEQUENCE: 30
uauugcacau uacuaaguug ca 22

-continued

```
<210> SEQ ID NO 31
<211> LENGTH: 22
<212> TYPE: DNA
<213> ORGANISM: Homo sapiens

<400> SEQUENCE: 31
gugaaauguu uaggaccacu ag                                              22

<210> SEQ ID NO 32
<211> LENGTH: 22
<212> TYPE: DNA
<213> ORGANISM: Homo sapiens

<400> SEQUENCE: 32 ucauuuugu gauguugcag cu                                               22

<210> SEQ ID NO 33
<211> LENGTH: 21
<212> TYPE: DNA
<213> ORGANISM: Homo sapiens

<400> SEQUENCE: 33
uugugcuuga ucuaaccaug u                                               21

<210> SEQ ID NO 34
<211> LENGTH: 22
<212> TYPE: DNA
<213> ORGANISM: Homo sapiens

<400> SEQUENCE: 34
uucaaguaau ccaggauagg cu                                              22

<210> SEQ ID NO 35
<211> LENGTH: 22
<212> TYPE: DNA
<213> ORGANISM: Homo sapiens

<400> SEQUENCE: 35
aaaguucuga gacacuccga cu                                              22

<210> SEQ ID NO 36
<211> LENGTH: 22
<212> TYPE: DNA
<213> ORGANISM: Homo sapiens

<400> SEQUENCE: 36
aguuuugcau aguugcacua ca                                              22

<210> SEQ ID NO 37
<211> LENGTH: 23
<212> TYPE: DNA
<213> ORGANISM: Homo sapiens

<400> SEQUENCE: 37
uguaguguuu ccuacuuuau gga                                             23

<210> SEQ ID NO 38
<211> LENGTH: 21
<212> TYPE: DNA
<213> ORGANISM: Homo sapiens

<400> SEQUENCE: 38
caacaccagu cgaugggcug u                                               21
```

```
<210> SEQ ID NO 39
<211> LENGTH: 21
<212> TYPE: DNA
<213> ORGANISM: Homo sapiens

<400> SEQUENCE: 39
cuauacaauc uacugucuuu c                                              21

<210> SEQ ID NO 40
<211> LENGTH: 22
<212> TYPE: DNA
<213> ORGANISM: Homo sapiens

<400> SEQUENCE: 40
cuauacaacc uacugccuuc cc                                             22

<210> SEQ ID NO 41
<211> LENGTH: 20
<212> TYPE: DNA
<213> ORGANISM: Homo sapiens

<400> SEQUENCE: 41
uacaguauag augauguacu                                                20

<210> SEQ ID NO 42
<211> LENGTH: 22
<212> TYPE: DNA
<213> ORGANISM: Homo sapiens

<400> SEQUENCE: 42
cugguacagg ccuggggac ag                                              22

<210> SEQ ID NO 43
<211> LENGTH: 22
<212> TYPE: DNA
<213> ORGANISM: Homo sapiens

<400> SEQUENCE: 43
caauuuagug ugugugauau uu                                             22

<210> SEQ ID NO 44
<211> LENGTH: 22
<212> TYPE: DNA
<213> ORGANISM: Homo sapiens

<400> SEQUENCE: 44
cagugcaaug uuaaaagggc au                                             22

<210> SEQ ID NO 45
<211> LENGTH: 21
<212> TYPE: DNA
<213> ORGANISM: Homo sapiens

<400> SEQUENCE: 45
uacaguacug ugauaacuga a                                              21

<210> SEQ ID NO 46
<211> LENGTH: 23
<212> TYPE: DNA
<213> ORGANISM: Homo sapiens

<400> SEQUENCE: 46
acugcccuaa gugcuccuuc ugg                                            23
```

-continued

```
<210> SEQ ID NO 47
<211> LENGTH: 22
<212> TYPE: DNA
<213> ORGANISM: Homo sapiens

<400> SEQUENCE: 47
cuauacgacc ugcugccuuu cu                                              22

<210> SEQ ID NO 48
<211> LENGTH: 21
<212> TYPE: DNA
<213> ORGANISM: Homo sapiens

<400> SEQUENCE: 48
cucacugaac aaugaaugca a                                               21

<210> SEQ ID NO 49
<211> LENGTH: 22
<212> TYPE: DNA
<213> ORGANISM: Homo sapiens

<400> SEQUENCE: 49
ugucaguuug ucaaauaccc ca                                              22

<210> SEQ ID NO 50
<211> LENGTH: 22
<212> TYPE: DNA
<213> ORGANISM: Homo sapiens

<400> SEQUENCE: 50
cuuaucagau uguauuguaa uu                                              22

<210> SEQ ID NO 51
<211> LENGTH: 22
<212> TYPE: DNA
<213> ORGANISM: Homo sapiens

<400> SEQUENCE: 51
cuauacggcc uccuagcuuu cc                                              22

<210> SEQ ID NO 52
<211> LENGTH: 22
<212> TYPE: DNA
<213> ORGANISM: Homo sapiens

<400> SEQUENCE: 52
ucgacagcac gacacugccu uc                                              22

<210> SEQ ID NO 53
<211> LENGTH: 22
<212> TYPE: DNA
<213> ORGANISM: Homo sapiens

<400> SEQUENCE: 53
aaucaugugc agugccaaua ug                                              22

<210> SEQ ID NO 54
<211> LENGTH: 23
<212> TYPE: DNA
<213> ORGANISM: Homo sapiens

<400> SEQUENCE: 54
agcucggucu gaggccccuc agu                                             23
```

-continued

<210> SEQ ID NO 55
<211> LENGTH: 22
<212> TYPE: DNA
<213> ORGANISM: Homo sapiens

<400> SEQUENCE: 55
cugugcgugu gacagcggcu ga                                              22

<210> SEQ ID NO 56
<211> LENGTH: 21
<212> TYPE: DNA
<213> ORGANISM: Homo sapiens

<400> SEQUENCE: 56
ugguucuaga cuugccaacu a                                               21

<210> SEQ ID NO 57
<211> LENGTH: 22
<212> TYPE: DNA
<213> ORGANISM: Homo sapiens

<400> SEQUENCE: 57
cggcaacaag aaacugccug ag                                              22

<210> SEQ ID NO 58
<211> LENGTH: 22
<212> TYPE: DNA
<213> ORGANISM: Homo sapiens

<400> SEQUENCE: 58 ucaccggug uaaaucagcu ug                                               22

<210> SEQ ID NO 59
<211> LENGTH: 22
<212> TYPE: DNA
<213> ORGANISM: Homo sapiens

<400> SEQUENCE: 59
auaaagcuag auaaccgaaa gu                                              22

<210> SEQ ID NO 60
<211> LENGTH: 22
<212> TYPE: DNA
<213> ORGANISM: Homo sapiens

<400> SEQUENCE: 60
uuuggucccc uucaaccagc ug                                              22

<210> SEQ ID NO 61
<211> LENGTH: 22
<212> TYPE: DNA
<213> ORGANISM: Homo sapiens

<400> SEQUENCE: 61
cuuucagucg gauguuugca gc                                              22

<210> SEQ ID NO 62
<211> LENGTH: 21
<212> TYPE: DNA
<213> ORGANISM: Homo sapiens

<400> SEQUENCE: 62
aucacauugc cagggauuuc c                                               21

```
<210> SEQ ID NO 63
<211> LENGTH: 22
<212> TYPE: DNA
<213> ORGANISM: Homo sapiens

<400> SEQUENCE: 63
cauugcacuu gucucggucu ga                                              22

<210> SEQ ID NO 64
<211> LENGTH: 22
<212> TYPE: DNA
<213> ORGANISM: Homo sapiens

<400> SEQUENCE: 64
caauuuagug ugugugauau uu                                              22

<210> SEQ ID NO 65
<211> LENGTH: 22
<212> TYPE: DNA
<213> ORGANISM: Homo sapiens

<400> SEQUENCE: 65
uugcauaguc acaaaaguga uc                                              22

<210> SEQ ID NO 66
<211> LENGTH: 22
<212> TYPE: DNA
<213> ORGANISM: Homo sapiens

<400> SEQUENCE: 66
augguuccgu caagcaccau gg                                              22

<210> SEQ ID NO 67
<211> LENGTH: 22
<212> TYPE: DNA
<213> ORGANISM: Homo sapiens

<400> SEQUENCE: 67
ccuauucuug guuacuugca cg                                              22

<210> SEQ ID NO 68
<211> LENGTH: 22
<212> TYPE: DNA
<213> ORGANISM: Homo sapiens

<400> SEQUENCE: 68
ucagugcacu acagaacuuu gu                                              22

<210> SEQ ID NO 69
<211> LENGTH: 23
<212> TYPE: DNA
<213> ORGANISM: Homo sapiens

<400> SEQUENCE: 69
ugugcaaauc uaugcaaaac uga                                             23

<210> SEQ ID NO 70
<211> LENGTH: 21
<212> TYPE: DNA
<213> ORGANISM: Rattus norvegicus

<400> SEQUENCE: 70
cauaaaguag aaagcacuac u                                               21
```

```
<210> SEQ ID NO 71
<211> LENGTH: 22
<212> TYPE: DNA
<213> ORGANISM: Rattus norvegicus

<400> SEQUENCE: 71
uagcuuauca gacugauguu ga                                              22

<210> SEQ ID NO 72
<211> LENGTH: 22
<212> TYPE: DNA
<213> ORGANISM: Rattus norvegicus

<400> SEQUENCE: 72
ugagguagua gguuguauag uu                                              22

<210> SEQ ID NO 73
<211> LENGTH: 22
<212> TYPE: DNA
<213> ORGANISM: Rattus norvegicus

<400> SEQUENCE: 73
ugagguagua gguugugugg uu                                              22

<210> SEQ ID NO 74
<211> LENGTH: 22
<212> TYPE: DNA
<213> ORGANISM: Rattus norvegicus

<400> SEQUENCE: 74
ugagguagua gauuguauag uu                                              22

<210> SEQ ID NO 75
<211> LENGTH: 23
<212> TYPE: DNA
<213> ORGANISM: Rattus norvegicus

<400> SEQUENCE: 75
ggauaucauc auauacugua agu                                             23

<210> SEQ ID NO 76
<211> LENGTH: 22
<212> TYPE: DNA
<213> ORGANISM: Rattus norvegicus

<400> SEQUENCE: 76
ucucccaacc cuuguaccag ug                                              22

<210> SEQ ID NO 77
<211> LENGTH: 22
<212> TYPE: DNA
<213> ORGANISM: Rattus norvegicus

<400> SEQUENCE: 77
uauugcacau uacuaaguug ca                                              22

<210> SEQ ID NO 78
<211> LENGTH: 22
<212> TYPE: DNA
<213> ORGANISM: Rattus norvegicus

<400> SEQUENCE: 78
gcucuuuuca cauugugcua cu                                              22
```

```
<210> SEQ ID NO 79
<211> LENGTH: 22
<212> TYPE: DNA
<213> ORGANISM: Rattus norvegicus

<400> SEQUENCE: 79
ucaguuauca cagugcugau gc                                                22

<210> SEQ ID NO 80
<211> LENGTH: 23
<212> TYPE: DNA
<213> ORGANISM: Rattus norvegicus

<400> SEQUENCE: 80
uaaggugcau cuagugcaga uag                                               23

<210> SEQ ID NO 81
<211> LENGTH: 22
<212> TYPE: DNA
<213> ORGANISM: Rattus norvegicus

<400> SEQUENCE: 81
agagguagua gguugcauag uu                                                22

<210> SEQ ID NO 82
<211> LENGTH: 23
<212> TYPE: DNA
<213> ORGANISM: Rattus norvegicus

<400> SEQUENCE: 82
aacauucauu gcugucggug ggu                                               23

<210> SEQ ID NO 83
<211> LENGTH: 23
<212> TYPE: DNA
<213> ORGANISM: Rattus norvegicus

<400> SEQUENCE: 83
cguguauuug acaagcugag uug                                               23

<210> SEQ ID NO 84
<211> LENGTH: 22
<212> TYPE: DNA
<213> ORGANISM: Rattus norvegicus

<400> SEQUENCE: 84
gccuucucuu cccgguucuu cc                                                22

<210> SEQ ID NO 85
<211> LENGTH: 22
<212> TYPE: DNA
<213> ORGANISM: Rattus norvegicus

<400> SEQUENCE: 85
auauaauaca accugcuaag ug                                                22

<210> SEQ ID NO 86
<211> LENGTH: 22
<212> TYPE: DNA
<213> ORGANISM: Rattus norvegicus

<400> SEQUENCE: 86
ugagguagga gguuguauag uu                                                22
```

-continued

```
<210> SEQ ID NO 87
<211> LENGTH: 22
<212> TYPE: DNA
<213> ORGANISM: Rattus norvegicus

<400> SEQUENCE: 87
uagguaguuu ccuguuguug gg                                              22

<210> SEQ ID NO 88
<211> LENGTH: 23
<212> TYPE: DNA
<213> ORGANISM: Rattus norvegicus

<400> SEQUENCE: 88
uuuggcacua gcacauuuuu gcu                                             23

<210> SEQ ID NO 89
<211> LENGTH: 24
<212> TYPE: DNA
<213> ORGANISM: Rattus norvegicus

<400> SEQUENCE: 89
ugaggggcag agagcgagac uuuu                                            24

<210> SEQ ID NO 90
<211> LENGTH: 22
<212> TYPE: DNA
<213> ORGANISM: Rattus norvegicus

<400> SEQUENCE: 90
agccacugcc cacagcacac ug                                              22

<210> SEQ ID NO 91
<211> LENGTH: 25
<212> TYPE: DNA
<213> ORGANISM: Rattus norvegicus

<400> SEQUENCE: 91
uuuggcaaug guagaacuca caccg                                           25

<210> SEQ ID NO 92
<211> LENGTH: 22
<212> TYPE: DNA
<213> ORGANISM: Rattus norvegicus

<400> SEQUENCE: 92
uagguaguuu cauguuguug gg                                              22

<210> SEQ ID NO 93
<211> LENGTH: 23
<212> TYPE: DNA
<213> ORGANISM: Rattus norvegicus

<400> SEQUENCE: 93
ucuuugguua ucuagcugua uga                                             23

<210> SEQ ID NO 94
<211> LENGTH: 22
<212> TYPE: DNA
<213> ORGANISM: Rattus norvegicus

<400> SEQUENCE: 94
agcugguaaa auggaaccaa au                                              22
```

```
<210> SEQ ID NO 95
<211> LENGTH: 22
<212> TYPE: DNA
<213> ORGANISM: Rattus norvegicus

<400> SEQUENCE: 95
uguaaacauc cucgacugga ag                                           22

<210> SEQ ID NO 96
<211> LENGTH: 22
<212> TYPE: DNA
<213> ORGANISM: Rattus norvegicus

<400> SEQUENCE: 96
acggguauuc uugggugga aa                                            22

<210> SEQ ID NO 97
<211> LENGTH: 22
<212> TYPE: DNA
<213> ORGANISM: Rattus norvegicus

<400> SEQUENCE: 97 ggggguuccug gggaugggau uu                                          22

<210> SEQ ID NO 98
<211> LENGTH: 22
<212> TYPE: DNA
<213> ORGANISM: Rattus norvegicus

<400> SEQUENCE: 98
aggcggagac acgggcaauu gc                                           22

<210> SEQ ID NO 99
<211> LENGTH: 22
<212> TYPE: DNA
<213> ORGANISM: Rattus norvegicus

<400> SEQUENCE: 99
uauugcacau uacuaaguug ca                                           22

<210> SEQ ID NO 100
<211> LENGTH: 21
<212> TYPE: DNA
<213> ORGANISM: Rattus norvegicus

<400> SEQUENCE: 100
agugguucuu aacaguucaa c                                            21

<210> SEQ ID NO 101
<211> LENGTH: 23
<212> TYPE: DNA
<213> ORGANISM: Rattus norvegicus

<400> SEQUENCE: 101
gucauuuuug ugauguugca gcu                                          23

<210> SEQ ID NO 102
<211> LENGTH: 21
<212> TYPE: DNA
<213> ORGANISM: Rattus norvegicus

<400> SEQUENCE: 102
uugugcuuga ucuaaccaug u                                            21
```

```
<210> SEQ ID NO 103
<211> LENGTH: 22
<212> TYPE: DNA
<213> ORGANISM: Rattus norvegicus

<400> SEQUENCE: 103
uucaaguaau ccaggauagg cu                                              22

<210> SEQ ID NO 104
<211> LENGTH: 22
<212> TYPE: DNA
<213> ORGANISM: Rattus norvegicus

<400> SEQUENCE: 104
gaaguucugu uauacacuca gg                                              22

<210> SEQ ID NO 105
<211> LENGTH: 20
<212> TYPE: DNA
<213> ORGANISM: Rattus norvegicus

<400> SEQUENCE: 105
ucguuuugca uaguugcacu                                                 20

<210> SEQ ID NO 106
<211> LENGTH: 23
<212> TYPE: DNA
<213> ORGANISM: Rattus norvegicus

<400> SEQUENCE: 106
uguaguguuu ccuacuuuau gga                                             23

<210> SEQ ID NO 107
<211> LENGTH: 22
<212> TYPE: DNA
<213> ORGANISM: Rattus norvegicus

<400> SEQUENCE: 107
caacagcagu cgaugggcug uc                                              22

<210> SEQ ID NO 108
<211> LENGTH: 22
<212> TYPE: DNA
<213> ORGANISM: Rattus norvegicus

<400> SEQUENCE: 108
cuauacaauc uacugucuuu cc                                              22

<210> SEQ ID NO 109
<211> LENGTH: 22
<212> TYPE: DNA
<213> ORGANISM: Rattus norvegicus

<400> SEQUENCE: 109
cuauacaacc uacugccuuc cc                                              22

<210> SEQ ID NO 110
<211> LENGTH: 21
<212> TYPE: DNA
<213> ORGANISM: Rattus norvegicus

<400> SEQUENCE: 110
cuauacaauc uauugccuuc c                                               21
```

<210> SEQ ID NO 111
<211> LENGTH: 20
<212> TYPE: DNA
<213> ORGANISM: Rattus norvegicus

<400> SEQUENCE: 111
uacaguauag augauguacu                                              20

<210> SEQ ID NO 112
<211> LENGTH: 19
<212> TYPE: DNA
<213> ORGANISM: Rattus norvegicus

<400> SEQUENCE: 112
cugguacagg ccuggggga                                               19

<210> SEQ ID NO 113
<211> LENGTH: 22
<212> TYPE: DNA
<213> ORGANISM: Rattus norvegicus

<400> SEQUENCE: 113
gcaauuuagu gugugugaua uu                                           22

<210> SEQ ID NO 114
<211> LENGTH: 22
<212> TYPE: DNA
<213> ORGANISM: Rattus norvegicus

<400> SEQUENCE: 114
cagugcaaug uuaaaagggc au                                           22

<210> SEQ ID NO 115
<211> LENGTH: 21
<212> TYPE: DNA
<213> ORGANISM: Rattus norvegicus

<400> SEQUENCE: 115
uacaguacug ugauaacuga a                                            21

<210> SEQ ID NO 116
<211> LENGTH: 21
<212> TYPE: DNA
<213> ORGANISM: Rattus norvegicus

<400> SEQUENCE: 116
acugcccuaa gugcuccuuc u                                            21

<210> SEQ ID NO 117
<211> LENGTH: 22
<212> TYPE: DNA
<213> ORGANISM: Rattus norvegicus

<400> SEQUENCE: 117
cuauacgacc ugcugccuuu cu                                           22

<210> SEQ ID NO 118
<211> LENGTH: 21
<212> TYPE: DNA
<213> ORGANISM: Rattus norvegicus

<400> SEQUENCE: 118
cucacugaac aaugaaugca a                                            21

```
<210> SEQ ID NO 119
<211> LENGTH: 21
<212> TYPE: DNA
<213> ORGANISM: Rattus norvegicus

<400> SEQUENCE: 119
ugucaguuug ucaaauaccc c                                              21

<210> SEQ ID NO 120
<211> LENGTH: 22
<212> TYPE: DNA
<213> ORGANISM: Rattus norvegicus

<400> SEQUENCE: 120
aaaagcuggg uugagagggc ga                                             22

<210> SEQ ID NO 121
<211> LENGTH: 22
<212> TYPE: DNA
<213> ORGANISM: Rattus norvegicus

<400> SEQUENCE: 121
cuuagcacgu uguauuauua uu                                             22

<210> SEQ ID NO 122
<211> LENGTH: 22
<212> TYPE: DNA
<213> ORGANISM: Rattus norvegicus

<400> SEQUENCE: 122
cuauacggcc uccuagcuuu cc                                             22

<210> SEQ ID NO 123
<211> LENGTH: 23
<212> TYPE: DNA
<213> ORGANISM: Rattus norvegicus

<400> SEQUENCE: 123
ucgacagcac gacacugccu uca                                            23

<210> SEQ ID NO 124
<211> LENGTH: 22
<212> TYPE: DNA
<213> ORGANISM: Rattus norvegicus

<400> SEQUENCE: 124
caaucaugug cagugccaau au                                             22

<210> SEQ ID NO 125
<211> LENGTH: 23
<212> TYPE: DNA
<213> ORGANISM: Rattus norvegicus

<400> SEQUENCE: 125
agcucggucu gaggccccuc agu                                            23

<210> SEQ ID NO 126
<211> LENGTH: 22
<212> TYPE: DNA
<213> ORGANISM: Rattus norvegicus

<400> SEQUENCE: 126
cugugcgugu gacagcggcu ga                                             22
```

```
<210> SEQ ID NO 127
<211> LENGTH: 22
<212> TYPE: DNA
<213> ORGANISM: Rattus norvegicus

<400> SEQUENCE: 127
ucggcaacaa gaaacugccu ga                                              22

<210> SEQ ID NO 128
<211> LENGTH: 22
<212> TYPE: DNA
<213> ORGANISM: Rattus norvegicus

<400> SEQUENCE: 128
auaaagcuag auaaccgaaa gu                                              22

<210> SEQ ID NO 129
<211> LENGTH: 22
<212> TYPE: DNA
<213> ORGANISM: Rattus norvegicus

<400> SEQUENCE: 129
uuuggucccc uucaaccagc ug                                              22

<210> SEQ ID NO 130
<211> LENGTH: 22
<212> TYPE: DNA
<213> ORGANISM: Rattus norvegicus

<400> SEQUENCE: 130
cuuucagucg gauguuugca gc                                              22

<210> SEQ ID NO 131
<211> LENGTH: 23
<212> TYPE: DNA
<213> ORGANISM: Rattus norvegicus

<400> SEQUENCE: 131
uuauugcuua agaauacgcg uag                                             23

<210> SEQ ID NO 132
<211> LENGTH: 21
<212> TYPE: DNA
<213> ORGANISM: Rattus norvegicus

<400> SEQUENCE: 132
aucacauugc cagggauuuc c                                               21

<210> SEQ ID NO 133
<211> LENGTH: 22
<212> TYPE: DNA
<213> ORGANISM: Rattus norvegicus

<400> SEQUENCE: 133
cauugcacuu gucucggucu ga                                              22

<210> SEQ ID NO 134
<211> LENGTH: 22
<212> TYPE: DNA
<213> ORGANISM: Rattus norvegicus

<400> SEQUENCE: 134
gcaauuuagu gugugugaua uu                                              22
```

```
<210> SEQ ID NO 135
<211> LENGTH: 22
<212> TYPE: DNA
<213> ORGANISM: Rattus norvegicus

<400> SEQUENCE: 135
gugaaauguu uaggaccacu ag                                              22

<210> SEQ ID NO 136
<211> LENGTH: 22
<212> TYPE: DNA
<213> ORGANISM: Rattus norvegicus

<400> SEQUENCE: 136
uugcauaguc acaaaaguga uc                                              22

<210> SEQ ID NO 137
<211> LENGTH: 21
<212> TYPE: DNA
<213> ORGANISM: Rattus norvegicus

<400> SEQUENCE: 137
aaacaugguu ccgucaagca c                                               21

<210> SEQ ID NO 138
<211> LENGTH: 21
<212> TYPE: DNA
<213> ORGANISM: Rattus norvegicus

<400> SEQUENCE: 138
ccuauucuug guuacuugca c                                               21

<210> SEQ ID NO 139
<211> LENGTH: 22
<212> TYPE: DNA
<213> ORGANISM: Rattus norvegicus

<400> SEQUENCE: 139
ucagugcauc acagaacuuu gu                                              22

<210> SEQ ID NO 140
<211> LENGTH: 23
<212> TYPE: DNA
<213> ORGANISM: Rattus norvegicus

<400> SEQUENCE: 140
ugugcaaauc uaugcaaaac uga                                             23
```